United States Patent
Johnson

(10) Patent No.: US 11,925,656 B2
(45) Date of Patent: Mar. 12, 2024

(54) BIOLOGICAL TOTAL JOINT REPLACEMENT

(71) Applicant: Lanny Leo Johnson, Henderson, NV (US)

(72) Inventor: Lanny Leo Johnson, Henderson, NV (US)

( * ) Notice: Subject to any disclaimer, the term of this patent is extended or adjusted under 35 U.S.C. 154(b) by 0 days.

(21) Appl. No.: 18/353,556

(22) Filed: Jul. 17, 2023

(65) Prior Publication Data

US 2023/0355648 A1    Nov. 9, 2023

Related U.S. Application Data

(63) Continuation-in-part of application No. 17/933,580, filed on Sep. 20, 2022, which is a continuation-in-part of application No. 15/839,491, filed on Dec. 12, 2017, now abandoned, which is a continuation of application No. 14/533,820, filed on Nov. 5, 2014, now abandoned.

(51) Int. Cl.
  *A61K 31/7048*   (2006.01)
  *A61K 31/192*    (2006.01)

(52) U.S. Cl.
  CPC ........ *A61K 31/7048* (2013.01); *A61K 31/192* (2013.01)

(58) Field of Classification Search
  None
  See application file for complete search history.

(56) References Cited

U.S. PATENT DOCUMENTS

| | | | |
|---|---|---|---|
| 4,997,850 A | 3/1991 | Kimura et al. | |
| 5,621,009 A | 4/1997 | Watanabe et al. | |
| 9,486,468 B2 | 11/2016 | Johnson | |
| 10,322,125 B2 * | 6/2019 | Boden | A61P 19/00 |
| 2002/0058614 A1 * | 5/2002 | Filvaroff | A61P 7/06 |
| | | | 514/6.5 |
| 2006/0147564 A1 | 7/2006 | Kim | |
| 2010/0196331 A1 | 8/2010 | Johnson | |

FOREIGN PATENT DOCUMENTS

CN         101306003 A     3/2011

OTHER PUBLICATIONS

Farid, R., Rezaieyazdi, Z., Mirfeizi, Z., Hatef, M. R., Mirheidari, M., Mansouri, H., . . . & Watson, R. R. (2010). Oral intake of purple passion fruit peel extract reduces pain and stiffness and improves physical function in adult patients with knee osteoarthritis. Nutrition research, 30(9), 601-606. (Year: 2010).*
Abouaitah et al., "Enhanced Activity and Sustained Release of Protocatechuic Acid, a Natural Antibacterial Agent, from Hybrid Nanoformulations with Zinc Oxide Nanoparticles", Int. J. Mol. Sci. 2021, 22, 5287.
Ahmed et al., "Biological evidence for the benefit of green tea and ECCG in arthritis " Curr. Rheumatol. Rev. (2009) vol. 5, pp. 259-265.
All references cited by applicant in parent U.S. Appl. No. 15/839,491 per 37 CFR 1.98(d)(1).
All references cited by applicant in parent U.S. Appl. No. 17/933,580 per 37 CFR 1.98(d)(1).
All references cited by applicant in parent U.S. Appl. No. 14/533,820 per 37 CFR 1.98(d)(1).
Alvarez-Soria, M. et al "Long term NSAI D treatment inhibits COX-2 synthesis . . . " Ann. Rheum. Dis. (2006) vol. 65, pp. 998-1005.
Anderson, D. et al "Post-traumatic osteoarthritis . . . " J. Orthopaed. Res., vol. 29, No. 6, pp. 802-809. (Year: 2011).
Attur, M. et al "Prostaglandin E2 exerts catabolic effects . . . " J. Immunol., vol. 181, pp. 5082-5088. (Year: 2008).
Bajpayee AG, Grodzinsky AJ., Abstract "Cartilage-targeting drug delivery: can electrostatic interactions help?", Nat Rev Rheumatol. 2017;13:183-93.
Bao, J. et al "Lubricin: a novel potential biotherapeutic . . . " Mol. Biol. Rep. (2011) vol. 38, pp. 2879-2885.
Chiusaroli, R. et al "Experimental pharmacology of glucosamine sulfate" Int. J. Rheumatol., vol. 2011, pp. 1-8. (Year: 2011).
D'Lima DD, Hashimoto S, Chen PC, et al., "Prevention of chondrocyte apoptosis", J Bone Joint Surg Am. 2001;83: S25-26.
Daher et al., "A Systematic Review of Oral Nutritional Supplement and Wound Healing", Annals of Otology, Rhinology & Laryngology 2022, vol. 131(12) 1358-1368.
Deighton, C. et al "Management of rheumatoid arthritis . . . " BMJ (2009) vol. 338, pp. 710-712.
Ding, Q. et al "Anti-arthritic effects of crocin . . . " Inflamm. Res. (2013) vol. 62, pp. 17-25.
Dougados, M.et al "Evaluation of the structure-modifying effects . . . " Arthritis & Rheumatism, vol. 44, No. 11, pp. 2539-2547. (Year:2001).
Goldberg, V. et al "Hyaluronans in the treatment of osteoarthritis of the knee: evidence for disease-modifying activity" , Osteoarth. Cartilage, vol. 13, pp. 216-224. (Year: 2005).
Grimberg A., "Mechanisms by which IGF-I may promote cancer", Cancer Biol Ther. 2003;2:6, 630-635.
Guyton et al., "Apparent spontaneous joint restoration in hip osteoarthritis", Clin Ortho Rel Res. 2002, #404;pp. 302-307.
Hayami, T. et al "Inhibition of cathepsin K reduces cartilage degeneration . . . " Bone, vol. 50, pp. 1250-1259 (Year: 2012).

(Continued)

*Primary Examiner* — Dale R Miller
(74) *Attorney, Agent, or Firm* — Stonebridge IP, PLLC

(57) ABSTRACT

The disclosure provides a method of joint repair or replacement in a mammal including surgically debriding a joint, administering a composition including a therapeutically effective amount of protocatechuic acid for between about 1 day and 1 month prior to arthroscopically debriding the joint, and administering the composition for between 1 day and 6 months after arthroscopically debriding the joint. The administration of the composition may be through oral administration. The composition may be a tablet, a pill, or a capsule. The tablet, the pill, or the capsule may include about 500 mg of protocatechuic acid.

13 Claims, 48 Drawing Sheets

(56) References Cited

OTHER PUBLICATIONS

Hickey DG, Frenkel SR, Di PC., Abstract "Clinical applications of growth factors for articular cartilage repair", Am J Orthop. 2003;32(2):70-76.
Hoemann et al., "International Cartilage Repair Society (ICRS) Recommended Guidelines for Histological Endpoints for Cartilage Repair Studies in Animal Models and Clinical Trials", Cartilage 2(2) 153-172.
Johnson et al., "Arthroscopic Abrasion Arthroplasty Historical and Pathological Perspective: Present Status", Arthroscopy Journal, 2:54-69, 1986.
Johnson et al., "The Long term clinical outcomes following autogenous bone grafting of large volume defects of the knee. 12- to 21-Year Follow-Up", Cartilage, Apr. 2014; vol. 5, Issue 2: pp. 86-96.
Johnson et. al., "The Pathology of the end-stage osteoarthritic lesion of the knee: Potential role in cartilage repair", Knee. 2011; 18(6). 402-406.
Jotanovic, Z. et al "Role of interleukin-1 inhibitors in osteoarthritis" Drugs Aging (2012) vol. 29, No. 5, pp. 343-358.
Koshino et al., "Regeneration of degenerated articular cartilage after high tibial valgus osteotomy for medial compartment osteoarthritis of the knee", Knee, Sep. 2003;10(3):229-36.
Krane et al., "Mechanisms of Matrix Degradation in Rheumatoid Arthritis", Department of Medicine Harvard Medical School and the Medical Services ( Arthritis Unit) Massachusetts General Hospital Boston, Massachusetts 02114.
Lende, A. et al "nti-inflammatory and analgesic activity of protocatechuic acid in rats and mice" Inflammopharmacol. (2011) vol. 19, pp. 255-263.
Li Y, Wang Y, Chubinskaya S, Schoeberl B, Florine E, Kopesky P, et al., "Effects of insulin-like growth Factor-1 and dexamethasone on cytokine-challenged cartilage: relevance to post traumatic osteoarthritis", osteoarthritis. 2015;23(2):266-274.
Lin, C-Y. et al "Antiglycative effects of protocatechuic acid . . . " J. Agric. Food Chem., vol. 59, No. 9, pp. 5117-5124, (Year: 2011).
Lutzner et al., "Surgical options for patients with osteoarthritis of the knee", Nature Reviews Rheumatology, vol. 5 Jun. 2009, 311.
M. P. J. van den Borne et al., "International Cartilage Repair Society (ICRS) and Oswestry macroscopic cartilage evaluation scores validated for use in Autologous Chondrocyte Implantation (ACI) and microfracture", Osteoarthritis and Cartilage (2007) 15, 1397-1402.
Malemud, C. "Anticytokine therapy for osteoarthritis" Drugs Aging (2010) vol. 27, No. 2, pp. 95-115.
Martin JA, Ellerbroek SM, Buckwalter JA., Abstract "Age-related decline in chondrocyte response to insulin-like growth factor-I: the role of growth factor binding proteins", J Orthop Res. 1997;15:491-8.
Medineplus, "Joint Disorder", retrieved on Sep. 15, 2022.
Milgram et al., "Morphologic alterations of the subchondral bone in advanced degenerative arthritis", Clin Orthop Relat Res. Mar. 1983; (173):293-312.
Min, S. et al "Anti-inflammatory effects of black rice . . . " Int. Immunopharmacol. (2010) vol. 10, pp. 959-966.
Morales TI, Hascall VC, "Factors involved in the regulation of proteoglycan metabolism in articular cartilage", Arthritis Rheum. 1989;32(10):1197-1201.
Noack, W. et al "Glucosamine sulfate in osteoarthritis . . . " Osteoarth. Cartilage, vol. 2, pp. 51-59. (Year: 1994).
Oh CD, Chun JS, "Signaling mechanisms leading to the regulation of differentiation and apoptosis of articular chondrocytes by insulin-like growth factor-1", J Biol Chem. 2003;278(38):36563-36571.
Pierre Mainil-Varlet, "Histological Assessment of Cartilage Repair: A Report By the Histology Endpoint Committee Ofthe International Cartilage Repair Society (ICRS)", The Journal of Bone and Joint Surgery, vol. 85-A supplement 2, Feb. 2003.
Pories et al., "Acceleration of Wound Healing in Man with Zinc Sulphate Given By Mouth", The Lancet, vol. 289, Issue 7482, Jan. 21, 1967, pp. 121-124.
Rudolphi, K. et al "Pralnacasan, an inhibitor of interleukin-1 b converting enzyme . . . " OsteoArthritis and Cartilage (2003) vol. 11,pp. 738-746.
Rutkute, K. et al "Regulation of insulin-like growth factor . . . " Biochem. Bio phys. Res. Comm. (2007) vol. 361, pp. 263-269.
Sandy J D, Lowther D A, Brown H L G, Abstract "Antigen-induced arthritis: studies on the inhibition of proteoglycan synthesis observed in articular cartilage during short-term joint inflammation", Arthritis Rheum 1980; 23: 433-47.
Schalkwijk, J. et al., ABSTRACT "Chondrocyte nonresponsiveness to insulin-like growth factor 1 in experimental arthritis", Arthritis and rheumatism, [s. l.], v. 32, n. 7, p. 894-900, 1989.
Scott et al., "Intravenous ibuprofen", Drugs 2012; 72 (8): 1099-1109.
Shakibaei M, Seifarth C, John J, et al, "Igf-I extends the chondrogenic potential of human articular chondrocytes in vitro: molecular association between Sox9 and Erk1/2", Biochem Pharmacol. 2006;2(11):1382-1395.
Snekhalatha, U. et al "Evaluation of complete Freund's adjuvant . . . " Z. Rheumatol. (2013) vol. 72, pp. 375-382.
T. L. McCarthy, M. Centrella, "Local IGF-I expression and bone formation", Growth Hormone & IGF Research 2001, 11, 213-219.
Van Den Berg et al., "Antigen-induced arthritis and zymosan-induced arthritis in mice: Studies on in vivo cartilage proteoglycan synthesis and chondrocyte death", BrJ Exp Pathol 1981; 62: 308-16.
Vedadghavami et al., "Cationic peptide carriers enable long-term delivery of insulin-like growth factor-1 to suppress osteoarthritis-induced matrix degradation", Arthritis Research & Therapy (2022) 24:172.
Wen et al., Insulin-like growth factor-1 in articular cartilage repair for osteoarthritis treatment, Arthritis Res Ther (2021) 23:277.
Wenham, C. et al "Methotrexate for pain relief in knee osteoarthritis . . . " Rheumatology (2013) vol. 52, pp. 888-892.
Wieland, H. et al "Osteoarthritis: an untreatable disease?" Nat. Rev. Drug Disc., vol. 4, pp. 331-344. (Year: 2005).
Wikipedia, "Arthropathy", the free encyclopedia, last edited on Jun. 10, 2022.
Wikipedia, "Arthroscopy", the free encyclopedia, retrieved on Jul. 7, 2023.
Wikipedia, "Debridement", the free encyclopedia, retrieved on Jul. 7, 2023.
Wikipedia, "Joint replacement", the free encyclopedia, retrieved on Jul. 7, 2023.
Wikipedia, "Preventive healthcare", the free encyclopedia, last edited on Sep. 14, 2022.
Wikipedia, "Protocatechuic acid", the free encyclopedia, last edited on Aug. 21, 2022.
Wikipedia, "Synovial joint", the free encyclopedia, last edited on May 19, 2022.
Wilkinson et al., "Does Oral Zinc Aid the Healing of Chronic Leg Ulcers?", Arch Dermatol, vol. 134, Dec. 1998, 1556-1560.
Zhang et al., "Cartilaginous deposits in subchondral bone in regions of exposed bone in osteoarthritis of the human knee: Histomorphometric study of PRG4 distribution in osteoarthritic cartilage", Journal of Orthopaedic Research. vol. 25, Issue 7, Date: Jul. 2007: 873-883.

\* cited by examiner

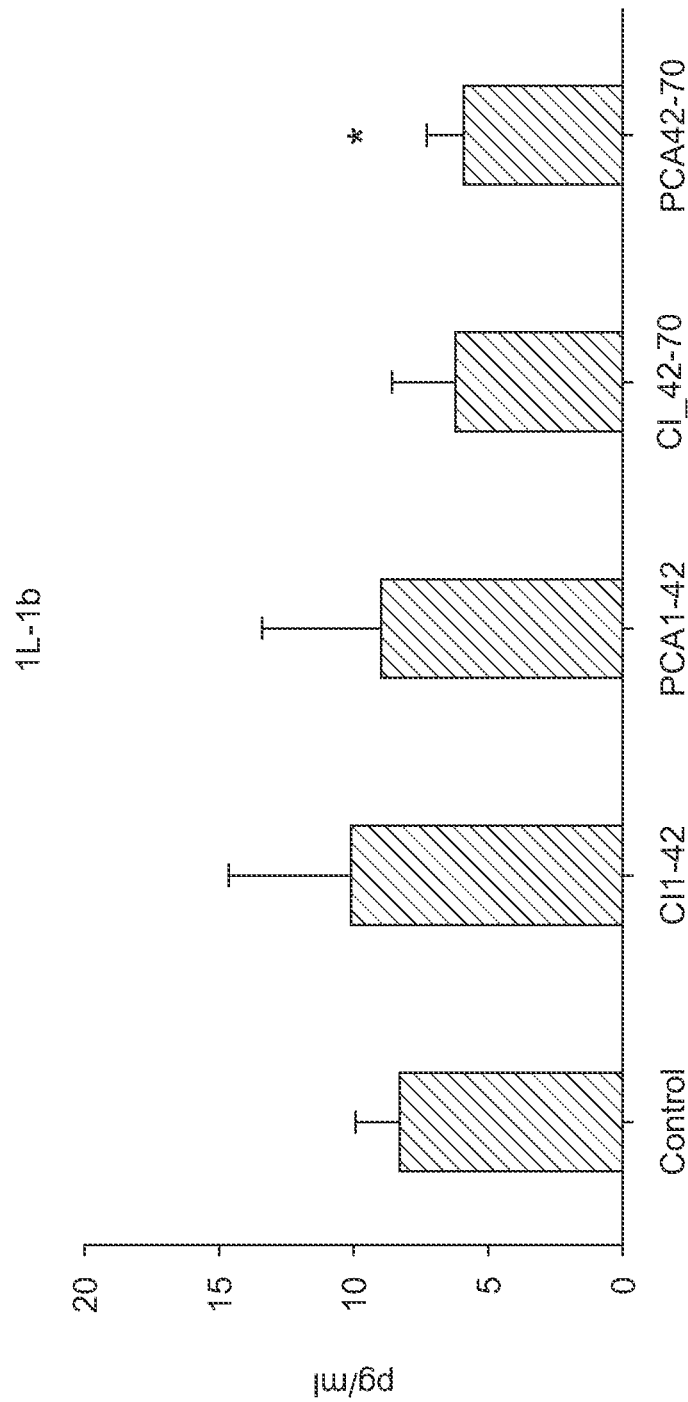

Figure 19: Lubricin expression was increased in the cartilage of all four groups Figure 21: ICRS histological visual scale. Surface scores improved for all groups Figure 22: ICRS histological visual scale. Matrix scores improved for all groups Figure 23: ICRS histological visual scale. Cell distribution improved for all groups Figure 24: ICRS histological visual scale. Cell viability remained the same for all groups Figure 25: ICRS histological visual scale. Subchondral bone score improved for all groups Figure 26: ICRS histological visual scale. Mineralization scores improved for all groups.

Figure 28: Il-10 Synovial Fluid

Figure 29: IL-4 Synovial Fluid

Phenolic acid (Vanillic acid) excretion in rabbits following oral gavage of control, cyanidin-3-glucoside (C-3-G)(10 mg/kg BW or Protocatechuic acid (3,4-dihydroxybenzoic acid) expressed as micrograms per mg creatinine in the urine sample Phenolic acid (Hippuric acid) excretion in rabbits following oral gavage of control, cyanidin-3-glucoside (C-3-G) (10 mg/kg BW or Protocatechuic acid (3,4-dihydroxybenzoic acid) expressed as micrograms per mg creatinine in the urine sample

BIOLOGICAL TOTAL JOINT REPLACEMENT

CROSS-REFERENCE TO RELATED APPLICATIONS

This application is a continuation in part of U.S. Ser. No. 17/933,580 filed on Sep. 20, 2022 which application is a continuation in part of U.S. Ser. No. 15/839,491, filed Dec. 12, 2017, which application is a continuation of U.S. Ser. No. 14/533,820, filed Nov. 5, 2014, with the disclosure of each of the above applications incorporated herein by reference in their entireties.

BACKGROUND OF THE INVENTION

The anatomy of a synovial joint consists of a variety of different tissues; bone, cartilage, and synovium. Bone on each side of the joint provides stability and proper alignment. The cartilage provides gliding motion. The synovium provides nutrition.

The joint may be affected by disease and/or injury. The pathological progression of a disease and/or injury is end stage arthritis with loss of motion and/or alignment. The bone may overgrow with osteophytes that limit the motion. The bone alignment may be altered in response to abnormal forces due to loss of the cushioning cartilage or result of a prior fracture. The cartilage will be lost over time due to inflammation causing a catabolic cytokine synovial fluid environment. The cartilage may be lost due to excessive loading of malalignment. The synovium is altered by inflammation from the debris and therefore is larger in volume while producing the catabolic cytokine environment of the synovial fluid. Independent of the etiology the end stage pathological condition is the same; deformed and dense bone, inflamed synovium and loss of articular cartilage exposing a sclerotic dead bone articular surface.

The natural history of the response to the end stage sclerotic articular surface is an aborted attempt at restoration. The blood supply proliferates up and into the sclerotic surface. Eventually there are aggregates of regenerated articular cartilage on the surface. The small foci of regenerative cartilage show histological evidence of hyaline cartilage.

However, the process is slow and never completely restores normal function. At this stage, no medication is known to benefit. Therefore, the present-day treatment is an artificial total joint replacement with metal and plastic which may return the patient to full activity in a few weeks. Total joint replacement has been a significant medical advancement for the end stage treatment of destructive joint disease. The implementation started with the hip joint, expanded to the knee and now most other joints; i.e., shoulder, elbow, wrist, ankle and more recently the spine. Tens of thousands cases have been performed and it has been projected that many more will be performed in the years to come due to the aging population. Total joint replacement has the prospect of reducing pain, increasing motion, increasing activities of daily living and importantly improving quality of life.

This surgery is not without complications, however, the worst of which is infection. There are also side effects. The implant and operation are also expensive and not all surgeries are successful. In the knee joint, even when function has been restored, there is a 25% dissatisfaction rate. Worse yet are the re-operations due to loosening, wear and/or infection. Although the reported infection rate is as low as 1 or 2% the results of such are devastating with high morbidity. The treatment is one or more surgeries over the course of one or more years. Long term antibiotics are necessary, and they are not without adverse side effects. Worse yet is the reported five-year mortality is as high as 25% which is higher than cancer of the breast and prostate. There is therefore a need in the art for a means to replace the end stage disease without metal and plastic parts; i.e., with a biological total joint.

SUMMARY OF THE INVENTION

This disclosure provides a method of joint repair or replacement in a mammal including surgically debriding a joint, administering a composition including a therapeutically effective amount of protocatechuic acid for between about 1 day and 1 month prior to arthroscopically debriding the joint, and administering the composition for between 1 day and 6 months after arthroscopically debriding the joint. The administration of the composition may be through oral administration. The composition may be a tablet, a pill, or a capsule. The tablet, the pill, or the capsule may include about 500 mg of protocatechuic acid.

The natural biological response to surgical debridement is bleeding, blood clot formation and undifferentiated fibrous tissue. If unchecked, the fibrous tissue or scar tissue will proliferate to the extent that it restricts joint motion. There is a need for the progression of healing to differentiate into specific tissues; synovium, bone, and cartilage. The natural biological response to differentiate into the various specific tissues is slow. The regeneration of the synovium will take a minimum of six weeks. Following removal of bony osteophytes, the superficial sclerotic dead bone surface will result in fibrocartilage repair in six months. A raw autogenous bone graft on an articulating surface will differentiate to articular cartilage over a period of many years. Although it is possible that the biological response may return the synovial joint to function following an extensive surgical debridement, the motion may be restricted by the fibrous tissue mass that did not progress to specific tissues. The natural healing response is slow and the return to activity can be prolonged.

Protocatechuic acid (PCA) provides a safe and effective means of accelerating the natural biological response and differentiation into specific synovial joint tissues. It is known that PCA will cause accelerated reepithelization of a mammalian skin wound with the production of collagen, so important to all structural healing. PCA is known in vitro to cause human osteoblasts and human mesenchymal stem cells to produce the foundation for restoration of bone. An oral prescription of 30 mg/kilogram or intraarticular injection of PCA can reduce mammalian synovial inflammation while increasing the local genetic anabolic growth factors; IGF-1, IL-4, IL-10. This results in the inflammatory catabolic cytokine presence in the synovial fluid to be reversed to one of anabolic cytokine presence.

The result on the articular cartilage is increased lubricin on the surface facilitating gliding motion. The cells are normal in structure, numbers and spacing. The matrix has increased aggrecan and type II collagen. The bone is normal without deforming osteophytes or increased density. The anabolic action of PCA by oral or intraarticular route will hasten the restoration and shorten the rehabilitation process. PCA will further promote regeneration by advancing the fibrous repair state to specific tissues.

The successful biological total joint is accomplished by enhancing the normal restoration process by surgical debridement that creates the foundation for the biological response. The addition of PCA shortens the healing time, while causing advancement to the specific synovial joint tissues; synovium, bone and cartilage.

The present invention provides oral formulations useful for treatment of an injured or diseased joint. PCA, a nutraceutical, can be taken to promote tissue, cartilage, synovium, and bone repair and regeneration. In embodiments, a course of administration can start before surgery of a joint occurs and continue on for a time period after a surgery. The formulations are as described herein below in more detail. In embodiments, the active ingredient comprises, consists essentially of, or consist of, protocatechuic acid (PCA).

Protocatechuic acid (PCA) is a phytochemical, a powerful antioxidant, which is found in nature. There are no known human toxic effects of PCA. PCA is non-allergenic. It is also non-mutagenic. Importantly, protocatechuic acid (PCA) has been designated as Generally Recognized As Safe (GRAS) by the FDA as a food flavoring substance. PCA may be biochemically manufactured and/or extracted from plants in an amorphous or crystalline state. See e.g., Protocatechuic acid, Wikipedia, the free encyclopedia, last edited: 21 Aug. 2022, herein incorporated by reference.

Methods of formulating pharmaceutical compositions are generally known in the art and are applicable with the invention. For instance, the active ingredient may be mixed with a pharmaceutically acceptable carrier or salt. Formulation development and selection of pharmaceutically acceptable excipients, carriers, stabilizers, coloring, and flavoring agents and the like and can be found in a variety of pharmaceutical texts known to those skilled in the art, such as Remington's Pharmaceutical Sciences (Mack Publishing Co., Eaton, Pa.).

In certain embodiments, the oral administration comprises administering a daily dose for at least 6 weeks of a dose of 0.177 mmoles PCA per kg body weight (26.4 mg/kg). In certain embodiments, the oral administration comprises administering a daily dose for at least 10 weeks of a dose of 0.177 mmoles PCA per kg body weight (26.4 mg/kg). The oral administration comprises administering a daily dose for at least 4 weeks of a dose 0.177 mmoles PCA per kg body weight (26.4 mg/kg) starting after the injury. The treatment can begin any time.

In certain embodiments, the oral administration comprises 0.177 mmoles PCA per kg body weight (26.4 mg/kg) and continuing on for some time after a surgery. As one illustrative example, the daily dose may begin at least one week before surgery and continue for at least 4 weeks after surgery at the same dose. In certain embodiments the oral daily dosage ranges from 0.035 to 0.100 millimoles PCA per kg of body weight. The oral daily dose can be given before surgery or before injury as a prophylactic treatment. The oral daily dose can be given during surgery and can be continued on after surgery or injury until the injury has healed. The oral daily dose can be given on a long-term basis as well.

In certain embodiments the oral daily dosage ranges from 0.100 to 0.200 mmol PCA per kg body weight. The oral daily dose can be given before surgery or before as a prophylactic treatment. The oral daily dose can be given during surgery and can be continued on after surgery. The oral daily dose can be given safely on a long-term basis for prophylactic reasons in anticipation of synovial joint deterioration due to injury and/or disease.

The present invention also provides a novel method that increases the genetic anabolic expression of IGF-1 in the synovial joint lining and synovial fluid and increases IGF-1 in the bloodstream. The result of this treatment is improved nutrition, protection, repair and regeneration of the articular cartilage in mammals. A composition including administering protocatechuic acid by the oral route thereby biologically increases the genetic anabolic expression of IGF-1 in the synovial joint lining. The resultant increased amount of IGF-1 in the synovial fluid bathes the articular cartilage, thereby providing protective nutrition to the articular cartilage.

Therefore, oral administration of PCA provides an unexpected result that is due, at least in part, to the method of delivery not being direct application to the cartilage by intraarticular injection (of IGF-1). The reason is the indirect increase of IGF-1 from the PCA oral route via blood to the synovial joint, action in harmony with the natural biological process of producing IGF-1 in the synovium by causing enhanced genetic expression of IGF-1. It does not require a prescription of multiple intraarticular injections over a period of time which is not always practical when translated to clinical medicine.

The present invention thus provides a method of improving the catabolic/anabolic state of an inflamed joint in a mammalian subject, by orally administering to the subject a composition of the present invention. The improved catabolic/anabolic state is brought about by a process selected from the group consisting of reduction of levels of MMP3, MMP-1, MMP13, IL-1B, TGF-beta, TNF-alpha, ADAMTS-5, in synovial fluid or synovium; and/or an increase of levels of IGF-1, lubricin, TIMP-1, VEGF, 11-10, IL-4, collagen II and/or aggrecan in synovial fluid or synovium of the inflamed joint.

The present invention also provides a method of decreasing the numbers of macrophages, lymphocytes and polymorphonuclear leukocytes in synovial fluid of an inflamed joint by orally administering to a subject a composition as described herein.

The invention also provides a method of treating an injured or arthritic joint by promoting healing of the cartilage of the joint in a mammalian subject, by orally administering to the subject a composition described herein, wherein the composition has the effect of increasing in the cartilage of the injured or arthritic joint expression levels of lubricin, aggrecan and collagen II to promote healing and to treat the injured or arthritic joint.

The invention also provides a method of decreasing levels of C reactive protein (CRP) in the plasma in a subject having an inflamed or injured joint, by orally administering to the subject a composition as described herein wherein the administration has the effect of decreasing levels of CRP in the plasma of the subject.

Also described herein is a method of providing a prophylactic treatment to a subject to reduce inflammation, wherein a composition of the invention is provided to the subject in advance of a surgery to the joint. The treatment may continue during the surgery as well as after the surgery. Further described herein is a method of providing a therapeutic treatment to a subject after surgery, wherein a composition of the invention is provided to the subject after surgery or injury to the joint.

Other features and aspects will be apparent from the following detailed description, the drawings, and the claims.

BRIEF DESCRIPTION OF DRAWINGS

FIG. 9A shows that levels of IL-1 beta were decreased in the synovium of the C3G and PCA therapeutic groups but were increased in the two prophylactic groups.

FIG. 32A is for 3,4-HBA excretion. FIG. 32B is for Vanillic acid and 32C is for Hippuric acid.

Figure legends:

Figure 1:
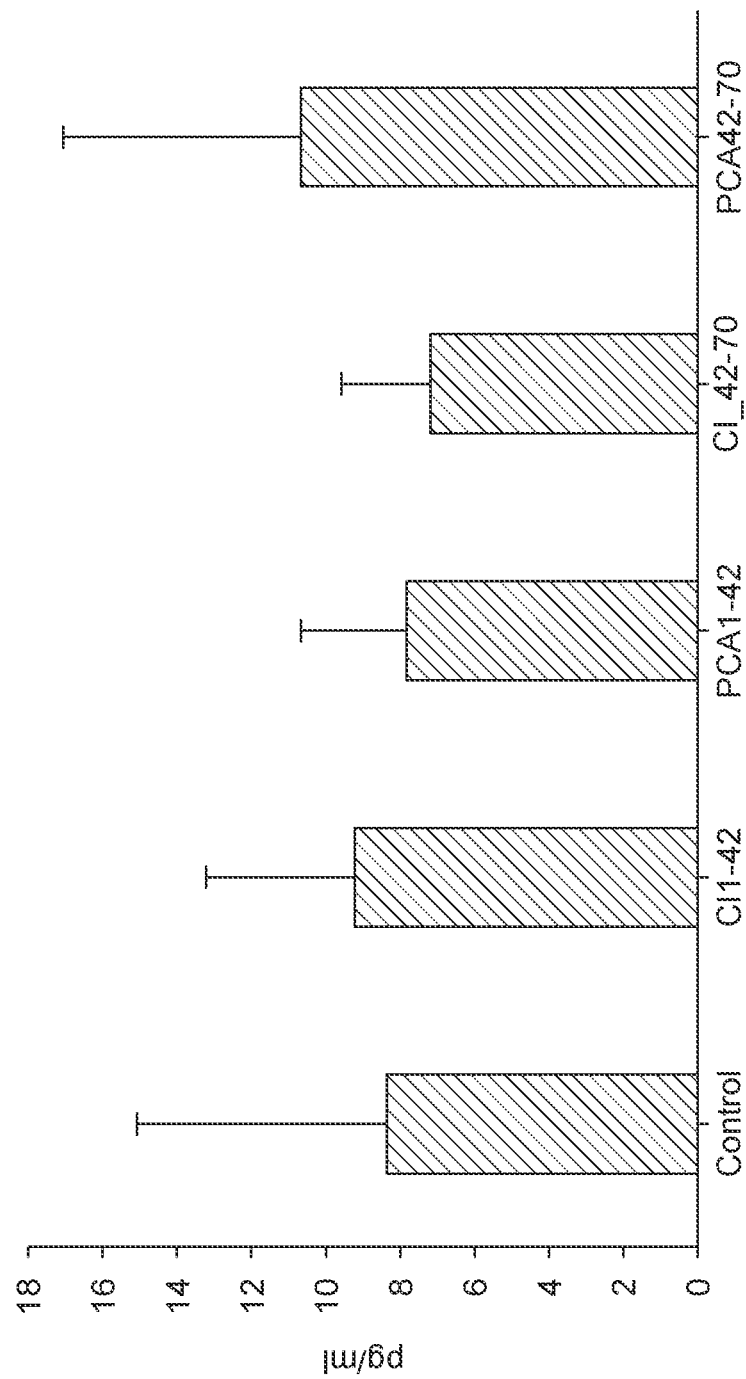
FIG. 1 (synovium) shows that MMP-13 levels were slightly decreased in the C3G therapeutic group and very slightly decreased in the PCA prophylactic group. The levels seemed to be increased slightly in the PCA therapeutic and the C3G prophylactic group. However, the levels of change appear not to be statistically significant.

Control: test subject did not receive any medication.

Cl 1-42: prophylactic C3G group (test subjects received 30 mg C3G/kg Body weight ("BW") Chromadex Pro3CG™ by mouth 7 times per week for 42 days). PCA 1-42: prophylactic PCA group (test subjects received 26.4 mg (PCA)/kg BW by mouth 7 times per week for 42 days). C142-70: Therapeutic C3G group (test subjects received 30 mg (C3G)/kg of body weight Chromadex™ Pro3CG™ by mouth (starting on day 42 after surgery through day 70) 7 times per week for 4 weeks. PCA 42-70: Therapeutic PCA group (test subjects received 26.4 mg (PCA)/kg bodyweight by mouth (starting on day 42 after surgery through day 70) 7 times per week for 4 weeks.

DETAILED DESCRIPTION OF THE INVENTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

The structure and biology of articular cartilage of the synovial joint is unique among the tissues of the human mammalian body. It is defined as hyaline cartilage to differentiate it from fibrous cartilage as in a meniscus or elastic cartilage that is in the ear or costal cartilage which is more cellular with type I cartilage.

Articular cartilage of the hyaline nature is found in the synovial joint. Unlike most tissues it has no resident blood supply. It receives nutrition by diffusion from the synovial fluid and the supporting subchondral bone. It consists primarily of water suspended in a fibrous network identified as aggrecan and the unique type II collagen. The main bulk of the structure is identified as the extra cellular matrix (ECM). Cells are singular, sparse, and widely distributed, and imbedded in the matrix.

The articular cartilage function is to support the joint integrity while promoting motion between two bones by the ECM mass. The motion is facilitated by lubricin, a unique surface lubricating protein. Lubricin's properties facilitate a smooth gliding motion between bones. The matrix mass by nature provides a cushioning effect to the loads transmitted across the synovial joint whether in motion or stationary. Articular cartilage is vulnerable to disruption due to injury, disease, or by genetic predisposition. One of the measures of disruption is the death of cartilage cells; apoptosis, which happens with injury.

The pathophysiology of disruption is the same, independent of the etiology. The first event is breakdown of the ECM by physical disruption or a fissure. Then fragmentation progresses to the surface whereby loose fragments are loosed into the synovial fluid. From there a vicious cycle results in progression of articular cartilage destruction.

Therefore, there is a need to support and optimize articular cartilage prior to and following surgery, injury, disease, or genetic predisposition. Absent the blood supply and with few widely spaced cells, the articular cartilage has limited repair or regenerative potential. It is totally dependent upon nutrition from the synovial fluid and the subchondral bone to maintain its integrity.

The art only references treatments. The treatments using IGF-1 are by in vitro topical application and/or intra articular injection. The oral medications that are currently available are therapeutic and not prophylactic.

It has long been recognized in the medical literature that IGF-1 plays a major role in articular cartilage metabolism. However, to date, no prophylactic or therapeutic clinical treatment has been implemented involving IGF-1. Research literature supporting the potential treatment of articular cartilage has been based upon the exogenous application of IGF-1. There has not been a protective use of IGF-1 by endogenous biological stimulation. In spite of all the various therapeutic attempts, the present-day definitive treatment for end stage loss of joint function remains artificial total joint replacement. There is thus a need in the art to nurture and protect articular cartilage thereby reducing the risk of surgery for end stage conditions.

The present invention provides a novel method that relies on endogenous biological means, rather than an exogenous delivery of the growth hormone IGF-1 or any other reagent including PCA. The result of this treatment is improved nutrition and protection of the articular cartilage in mammals. Administering a phytochemical medication, protocatechuic acid, by the oral route thereby biologically increases the genetic anabolic expression of IGF-1 in the synovial joint lining. The resultant increased amount of IGF-1 in the synovial fluid bathes the articular cartilage, thereby providing prophylactic protective nutrition to the articular cartilage.

A pathological experimental model was chosen to establish PCA as a chondro-nutritive and chondroprotective prophylactic medication. This mode better demonstrated the chondro-nutritive and chondro-protective potential of PCA than an experimental model having a normal condition. The normal joint would not provide the same magnitude of potential change. The results confirmed the prophylactic benefit of prescription of a minimum of 30 mg/kilo gram body weight of protocatechuic acid by oral route. This resulted in an enhanced biological structure of the articular cartilage. Compared to the controls, the articular cartilage cells were unchanged in nature and spacing. There was increased EMC supporting aggrecan and type II collagen. There was increased lubricin on the surface. Importantly the subchondral bone remained normal in structure, without degenerative changes of sclerosis or osteophyte formation.

The Biological Total Joint is a novel approach to total joint replacement based upon regenerating bone and ligaments naturally. Native cellular, tissue and joint restoration follows arthroscopic debridement and autogenous bone grafting. In addition, there is long term survival of the tissue plus a clinical benefit.

Arthroscopic debridement can result in a spontaneous autogenous restoration of the articulating surfaces with natural product treatment including protocatechuic acid. This enhanced natural response can result in a biological repair that functionally meets the outcome criteria of a conventional total joint replacement.

In one example, the joint can be the end stage arthritic shoulder joint in a patient with intact or reconstituted neuromuscular integrity. The selection of the shoulder more easily employs the critical element of post-operative unloading than one of the lower extremity or the spine. Limiting the early post-operative activities to pendulum exercises will minimize the loading of the joint while mobilizing the joint. It is recognized that other joints may require a restoration of a structural element.

The procedure can be performed by the widely practiced arthroscopic surgical method. The existing motorized instrumentation (shaver) and cutting tools facilitate the debridement and restoration of the deformed joint architecture.

The surgical procedure is performed by arthroscopic methods of debridement of the inflamed synovium and the bony osteophytes. The bony architecture and geometry are restored to anatomical conformity. The articular end stage sclerotic lesion is superficially abraded to remove the dead osteons and expose the vascularity. The wound is prepared in such a manner to enhance the biological response.

In order to enhance the restoration of the deformed joint architecture, a nutraceutical, protocatechuic acid is used. In one specific embodiment, it can be supplied in 500 mg capsule form.

The subjects can be candidates for a total shoulder operation. The indication for surgery is that of a total joint replacement of the shoulder in a subject whose general health does not pose an otherwise risk. The standard medical history, physical, x-ray and laboratory testing is rendered or obtained.

A regimen of oral administration of protocatechuic acid, 500 milligram capsules, is instituted a week before surgery. Then 500-milligram capsules 4 times a day starting day after surgery. The post-operative duration could be 6 weeks.

The operation can be performed arthroscopically as an out-patient. Post-operative care includes pain management. Immediate post-operative x-ray of the joint will establish the index condition. Instructional physical therapy is initiated immediately but limited to pendulum exercises. Interval visits as clinically indicated. Range of motion activities increased based upon clinical recovery and x-ray evidence. Follow-up at least monthly for one year.

Long term results are monitored by clinical findings and radiological evidence including MRI that now has capacity to differentiate nature of the cartilage repair. Second look arthroscopy may be performed to document the tissue response.

Protocatechuic acid (PCA) is a nutraceutical reagent. PCA is a phytochemical and presently marketed as a nutraceutical. PCA is a benzoic acid common throughout nature. PCA is common to the human diet. PCA is produced in small amounts by the bacteria in human bowel. PCA is a powerful antioxidant; 10× more powerful than vitamin E. PCA is a powerful anti-inflammatory reagent. PCA is non-toxic, non-allergenic, and non-mutagenic. PCA is a broad-spectrum antibiotic, biofilm destroyer, and anti-viral reagent. PCA has anabolic effects on cells, tissues, and organs. PCA's physical targeting mode of action may keep it from being antibiotic resistant.

Protocatechuic acid has shown pharmacological enhancement of regeneration of cells and tissue based upon its anabolic properties. Protocatechuic acid (PCA) has an anabolic property that increases the genetic expression of local growth factors in human bone cells, human synovial explants, rabbit synovium and rodent skin lesions. In vitro studies, dose related, shows PCA causes human osteoblasts and human mesenchymal stem cells to produce bone making markers. PCA directly applied to human synovial explants results in increased IGF-1. In vivo studies in rabbits showed PCA by either oral or intraarticular route to increase IGF-1 genetic expression in the synovium as well as reversing the catabolic cytokine environment in a surgically created arthritic knee. Studies on tape-stripped rodent backs, contaminated with MRSA and *Pseudomonas*, disinfected the wound in 2 days. The amazing additional result was the re-epithelialization of the wound and production of collagen layer in the dermis.

The combination of a minimally invasive arthroscopic joint debridement that restores the geometry, followed by the known natural cellular and tissue reparative response, enhanced by protocatechuic acid's anabolic effect provides a first of its kind, the biological total joint.

The term "pharmaceutically acceptable carrier" as used herein refers to the acceptance or use of the carrier in the pharmaceutical industry. Preferably the carrier is approved by the Federal Drug Administration (FDA) for use in humans. Exemplary carriers include physiological solutions including but not limited to glucose, dextrose, normal saline, phosphate buffered saline (PBS) or Ringer's solution.

The term "therapeutically effective amount" as used herein refers to an amount of an active ingredient that produces the intended result.

The oral dose can include, but is not limited to a tablet, capsule, powder, powder reconstituted in a liquid suitable for ingestion. Pharmaceutically acceptable carriers, preservatives, emulsifiers, stabilizers and other additives may be added.

The present invention provides a formulation useful in a method of decreasing inflammation of a joint in a mammalian subject. The present invention also provides methods of decreasing inflammation of a joint in a mammalian subject. The inflammation in the joint can be from an injury or trauma (including post-surgery inflammation) or from arthritis. Thus the joint can be injured or can be an arthritic joint.

Methods involve orally administering to the subject a composition comprising an active ingredient including protocatechuic acid (PCA). In one embodiment, the PCA is present at about 97% of the total active ingredient.

In the present invention, in certain embodiments the dose is 25-30 mg/kilogram of bodyweight. In certain embodiments the duration of the treatment is for 6 weeks and the dose is given 7 days per week. In certain embodiments, the duration of treatment is for 4 weeks and the dose is given 7 days per week. In certain embodiments, the treatment regimen starts immediately after injury and proceeds for at least 6 weeks. In certain embodiments the treatment regimen starts 6 weeks after injury and proceeds for at least 4 weeks. In certain embodiments, the treatment regimen starts immediately after injury and proceeds for at least 10 weeks.

In certain embodiments, the route of administration is oral. Powdered active ingredient can be mixed with a suitable liquid for drinking or gavage or alternatively, the active ingredient can be in the form of a pill or capsule. The active ingredient may also be mixed with other solid eatable ingredients, such as for an example, in a nutrition/snack bar.

In certain embodiments, the treatment is provided before surgery as a prophylactic treatment or prophylactic nutraceutical. In certain therapies, the treatment is continued to be provided for at least 6 weeks after the surgery. In certain embodiments, the treatment is every day.

In certain embodiments, the treatment is provided after surgery. In certain embodiments the treatment is a peri-surgical treatment (during surgery) or in conjunction with surgery.

In certain embodiments the oral formulation/treatment is given to a subject as an over the counter oral nutraceutical where the subject has existing arthritis or an existing joint injury who is suffering from inflammation in the joint.

The surgical procedure is preferably minimally invasive arthroscopy. Debridement is a common arthroscopic surgical practice. Arthroscopic instrumentation exists for bone removal of deforming osteophytes and for recontouring the articulating surfaces. The release of bone and or soft tissue restores the lost range of motion of the joint.

The biological response to arthroscopic debridement of the joint surfaces, removes the thin layer dead bone and exposes the superficial blood vessels. This creates a living tissue bed of bone for blood clot formation. A blood clot formation is the first biological event for spontaneous healing in the body; i.e., skin, muscle, bone, heart, lungs, liver, or intestine. It is also the first event following arthroscopic surgery, i.e., cartilage healing. It is a spontaneous biological response that any cut articular surface will attract a blood clot to be "held and hold" in situ.

Minimally invasive arthroscopy provides for natural repair of articular surfaces. Arthroscopic abrasion arthroplasty is typically for end stage arthritis. This procedure debrides the superficial dead bone layer and exposes the superficial vessels thereby forming a blood clot to form a matrix to initiate healing.

Another endogenous cartilage reparative procedure is microfracture. It is indicated for isolated well-defined avulsions of articular cartilage secondary to trauma, often a ligament injury.

Both procedures can repair articular surfaces, by second look arthroscopy and biopsy. Both surgical procedures are followed by early fibrocartilage articular cartilage repair that endures many years.

In embodiments, the administration of protocatechuic acid provides anabolic methods that stimulate or induce bone regeneration and repair, while also protecting against degradation of bone. Further, the administration of protocatechuic acid provides methods and compositions that deliver osteogenic activity.

In embodiments, the administration of PCA provides the promotion of osteogenic gene expression. In some embodiments, the therapeutically effective amount comprises at least 10 μM. In some embodiments, one or more cells are selected from the group consisting of mesenchymal stem cells (MSCs), adipose tissue-derived stem cells (ADSCs), endothelial progenitor cells (EPCs), mesenchymal skeletal stem cells (SSCs), synovial stem cells, bone marrow extract, osteoblasts, chondrocytes, and osteocytes and combinations thereof. In some embodiments, one or more cells are derived from autogenic, allogenic or xenogenic sources.

A Biological Total Joint as used herein refers to a type of total joint replacement that does not include the use of replacement (typically metal and plastic) prosthetic components. See e.g., Joint Replacement, Wikipedia, the free encyclopedia, downloaded Jul. 7, 2023, herein incorporated by reference. Biological total joint replacement typically involves an arthroscopic debridement procedure along with tissue and bone regeneration enhancement by a nutraceutical. In embodiments, the nutraceutical is protocatechuic acid.

Arthroscopy or arthroscopic surgical methods refer to minimally invasive surgical procedures on a joint in which an examination and sometimes treatment of damage is performed using an arthroscope, an endoscope that is inserted into the joint through a small incision. See Arthroscopy, Wikipedia, the free encyclopedia, downloaded Jul. 7, 2023, herein incorporated by reference.

Debridement is the medical removal of dead, damaged, or infected tissue, synovium, cartilage, or bone which can effect the healing of the remaining healthy tissue, synovium, cartilage, or bone. Removal may be surgical, mechanical, chemical, or autolytic. See Debridement, Wikipedia, the free encyclopedia, downloaded Jul. 7, 2023, herein incorporated by reference. Arthroscopic debridement refers to debridement performed arthroscopically.

The term chondroprotective or chondroprotective agent as used herein refers to a process, substance or molecule that inhibits or reduces the degradation of cartilage or chondrocytes. The compositions also increased the all-important surface lubricant, lubricin, which promotes joint surface gliding, thereby reducing peak axial loads on the articular cartilage.

Compositions comprising protocatechuic acid may further comprise zinc or a zinc supplement or zinc compound. For example, the zinc may be a zinc oxide or a zinc sulfate. The compositions may also contain sustained release compositions including protocatechuic acid and optionally including zinc, zinc oxide, or zinc sulfate. For example, the sustained release formulations may include nanoparticles of zinc including zinc oxide and protocatechuic acid.

In some embodiments, the composition includes a bone supplement selected from the group consisting of calcium, vitamin D, magnesium, and vitamin K and combinations thereof. In some embodiments, the compositions is formulated into a dosage form, the dosage form comprising a tablet, soft capsule, softgel, or liquid.

The term chondronutritive or chondronutritive agent as used herein refers to a process, substance or molecule that activates a cartilage cell to produce or enhances the production of glucopolysaccharides. The compositions of the invention are chondronutritive in that they increase the production of type II collagen, aggrecan and lubricin in the synovium.

The term chondroreparative or chondroreparative agent as used herein refers to a process, substance or molecule that causes cartilage to repair, such as with fibrocartilage. The compositions of the invention are chondroreparative because they increased the IGF-1 in the synovium and synovial fluid. IGF-1 arrests programmed cell death, apoptosis. In addition, the compositions by way of optimizing the anabolic/catabolic nature of the synovial joint environment, they thereby maximize the chondronutrition and chondroprotection for cartilage healing by the increase in IGF-1 presence and, in the case of surgery (open or arthroscopic) or arthrocentesis the presence of bleeding providing blood, a common denominator for wound healing.

The term chondrorestorative agent as used herein refers to a process, substance or molecule that causes cartilage to be restored to its normal hyaline pattern or nature. A chondrorestorative agent restores or improves normal activities or functions to the cartilage. The compositions of the invention provide the optimal environment for chondrorestoration.

The terms prophylactic or prophylaxis refers to action taken for the purpose of disease or injury prevention. See e.g., preventative healthcare, Wikipedia, the free encyclopedia, last edited: 14 Sep. 2022, herein incorporated by reference.

The terms disease or injury of a joint refers to conditions and injuries that affect joints including conditions developed as a result of age and overuse as well as sudden injuries from accidents or a sports injury. See Athropathy, Wikipedia, the free encyclopedia, last edited: 10 Jun. 2022, herein incorporated by reference; and joint disorders, MedlinePlus, last updated Dec. 13, 2021, herein incorporated by reference.

The term synovial joint, also known as diarthrosis, joins bones or cartilage with a fibrous joint capsule that is continuous with the periosteum of the joined bones, constitutes the outer boundary of a synovial cavity, and surrounds the bones' articulating surfaces. The synovial cavity/joint is filled with synovial fluid. The joint capsule is made up of an outer layer of fibrous membrane, which keeps the bones together structurally, and an inner layer, the synovial lining or membrane, which seals in the synovial fluid. See synovial joint, Wikipedia, the free encyclopedia, last edited: 19 May 2022, herein incorporated by reference.

The term "endogenously refers to being produced or synthesized from within an organism or system.

International Cartilage Repair Society (ICRS) criteria are described for example in Hoemann, et al., (cited on Applicant's IDS), herein incorporated by reference.

The Examples below demonstrate that protocatechuic acid given as an oral medication provided nutrition and protection of the articular cartilage of a mammalian synovial joint.

EXAMPLES

Example 1—Oral Ingestion Rabbit Study

The study was approved by the Institutional Animal Care and Use Committee (IACUC) of Thomas D. Morris, Inc. 28 New Zeeland White rabbits were selected for the study. Six such were randomly assigned to one of four groups; prophylactic cyanidin-3-glycoside (C3G)(referred to figures as Cl 1-42), prophylactic protocatechuic acid (PCA)(referred to in figures as PCA 1-42), therapeutic C3G (referred to in figures as Cl 42-70), and therapeutic PCA (referred to in figures as PCA 42-70). There were four controls, two each to the prophylactic and therapeutic groups. The controls did not receive any treatment.

The prophylactic groups were given PROC3G™ by Chromadex™ at a dose of 30 mg/kg of body weight of either C3G or PCA by mouth, 7 times per week for 42 days. The therapeutic groups' treatment was initiated on day 42 with a daily dose of PROC3G™ by Chromadex™ 7 times per week for 4 weeks. The dose of 30 mg of cyanidin-3-glucoside per kg of body weight calculates to be 0.177 millimoles per kg body weight. The dose of PCA was the same in terms of millimoles per kg body weight.

The experimental rabbits underwent surgery with an intent to create a severe degenerative arthritis by cutting the medial collateral ligament, the anterior cruciate ligament and removing the medial meniscus. A partial thickness laceration was made longitudinally on the lateral femoral condyle for future assessment of potential for repair. The surgery was performed by two licensed veterinarians. One surgeon was very experienced. The other surgeon was a recent graduate.

The magnitude of the arthritis was intentional in order to produce abundance of synovial reaction and synovial fluid for subsequent study. The experimental model was not designed for the likelihood of healing or cartilage repair due to the short time frame of the study.

At necropsy, the synovial fluid was harvested percutaneously and upon arthrotomy. The synovium was harvested from posterior compartment. The patella and adjacent synovium was procured as a separate specimen as was the medial and lateral condyle.

The synovial fluid and half of the synovium was frozen and sent to BioBoston Laboratory for chemical analysis. The other half of the synovium and bone was sent to McClinchery Histology in Stockbridge, Mich. for histological preparation and staining. Patellar slides were sent to BioBoston Contract Laboratories for histochemical staining and ICRS grading. Sample slides were examined for Lubricin at Myron Spector laboratory.

The cartilage status was subjected to a histological scale rating according to the International Cartilage Repair Society. Mainil-Varlet P, et al., The International Cartilage Repair Society (ICRS)-Histological Visual Scale. A preliminary Report of the Histological End Point Committee. I. Human Biopsies, Toronto Consensus. Europ Cells and Materials. Vol 4., Suppl. 1, 2002. (page 10).

Blood testing was performed prior to necropsy on C3G, PCA, glucose, MMP-3 and IGF-1 to assess any systemic effects.

Urine testing was performed prior to necropsy for C3G and PCA to assess the metabolic course. All reviews were performed by a blinded examiner.

Results

There were 20 rabbits available for bilateral tissue harvest. Four had partial tissue available (#9, 2, 8, and 15). There was no tissue on three; #1, 20, 28. One of the controls (#27) for the therapeutic groups required early euthanasia due to illness. One of the PCA (#10) therapeutic group was lost due to illness. One of the C3G therapeutic group (#28) died in recovery and another died during the course of the study. Three others specimens were compromised by dislocated knee in one case and dislocated patella in two. The surgery in the compromised animals was performed by the recent graduate licensed veterinarian.

There were 40 specimens sent from 20 rabbits for bilateral chemical analysis. There were three unilateral specimens. There were no specimens sent for histology on four animals; 10 #16, 20, 22, 28. Partial specimens were sent on #10 and 15.

There was no evidence of healing of the lateral femoral condylar surgically induced partial thickness laceration within the short duration of the study.

Various assays were performed to determine levels of certain biomolecules associated with inflammation (e.g. proinflammatory cytokines), anabolic or catabolic processes (e.g. IGF-1, EGF, TIMP, MMP-3, MMP-1, Adamts-5). These tests results are provided below.

MMP-3

MMP3 is known as matrix metallopeptidase 3, or stromelysin 1 or progelatinase. Proteins of the matrix metalloproteinase (MMP) family are involved in the breakdown of 20 extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases.

Synovial Fluid—Detected by ELISA

Figure 2A:
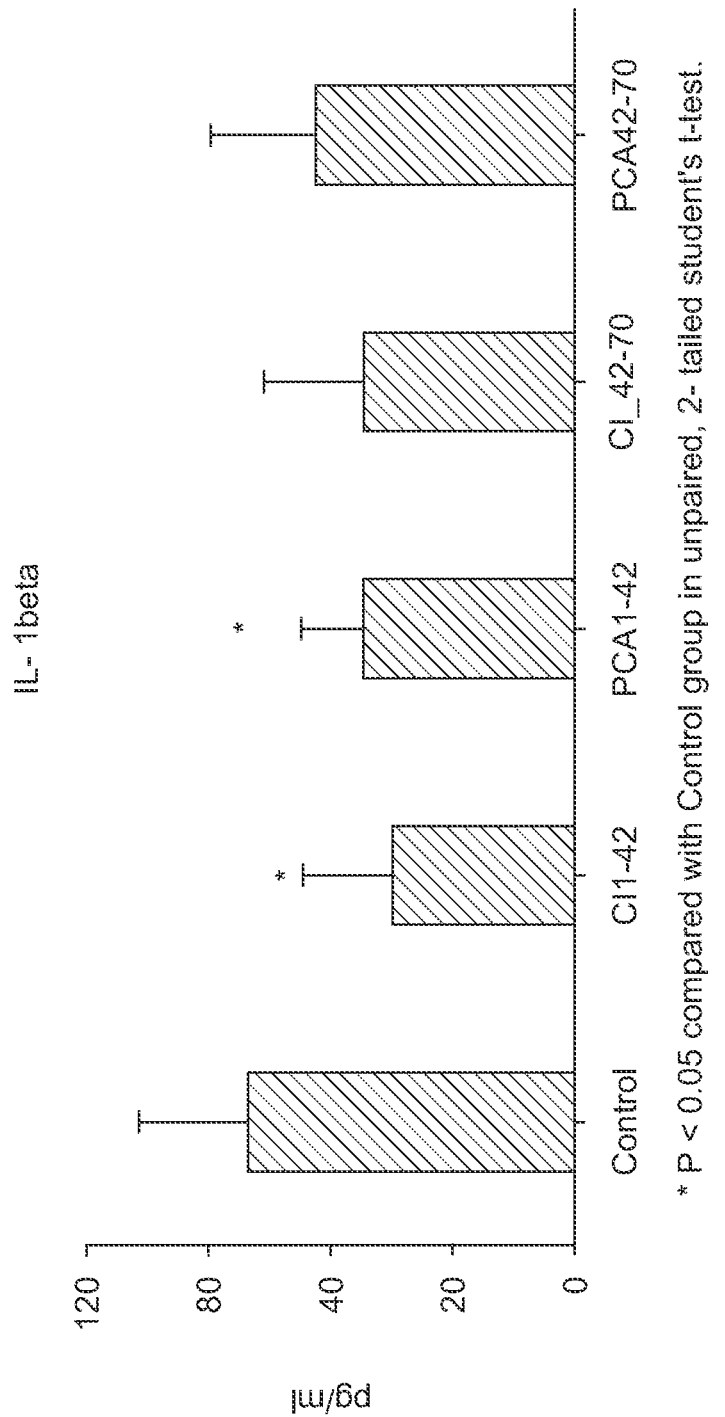
FIG. 2A shows that levels of IL-1 beta were decreased in the synovial fluid in all groups.
Figure 2B:
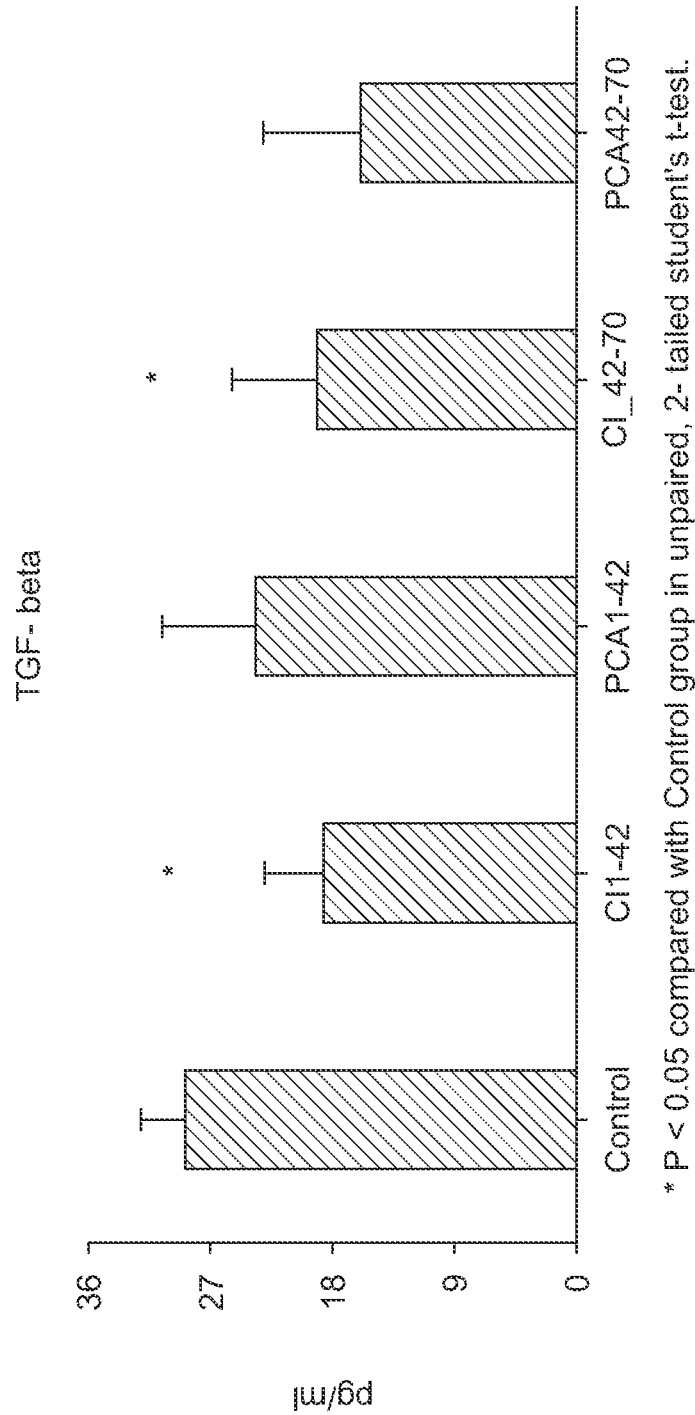
FIG. 2B shows that TGF-beta was decreased in the synovial fluid in all groups.
Figure 2C:
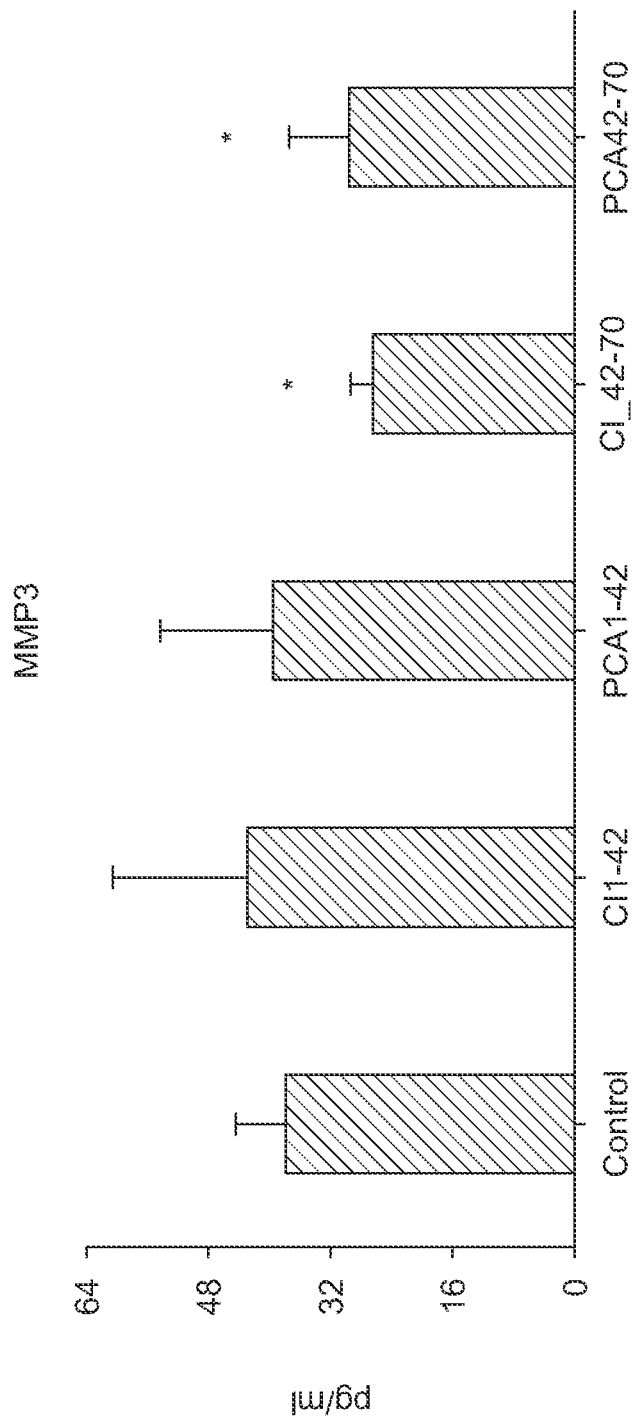
FIG. 2C shows that MMP3 was decreased in the synovial fluid for therapeutic groups for C3G and PCA.

MMP3 was decreased in the therapeutic groups for C3G and PCA. See FIG. 2C.

Synovial Tissue (Synovium)—Detected by ELISA

Figure 9B:
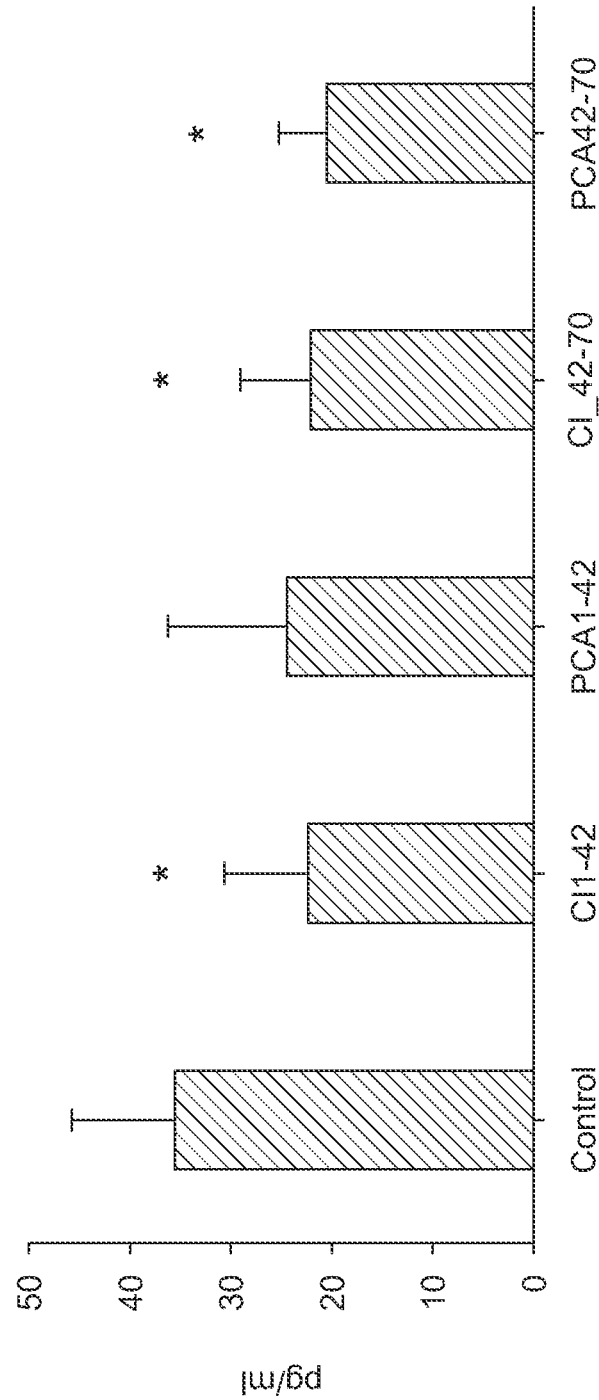
FIG. 9B shows that MMP-3 levels were reduced the synovium in all four groups.

MMP-3 levels were reduced in all four groups. See FIG. 9B.

Synovial Tissue (Synovium)—Gene Expression Level Detected by Real-Time PCR

Figure 13A:
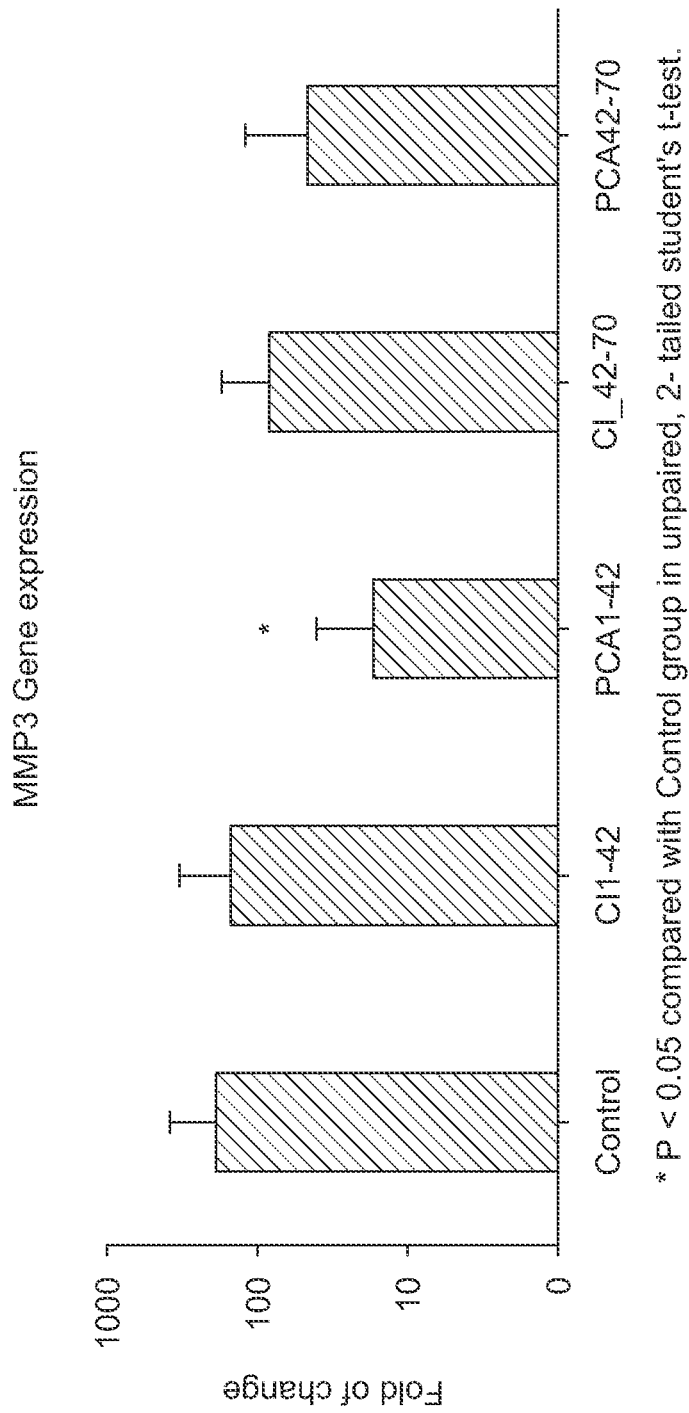
FIG. 13A shows that MMP-3 gene expression was decreased in the synovium as detected by real time PCT in all groups.

MMP-3 gene expression was decreased in all groups. See FIG. 13A.

Histochemical Scoring Analysis

Figure 3:
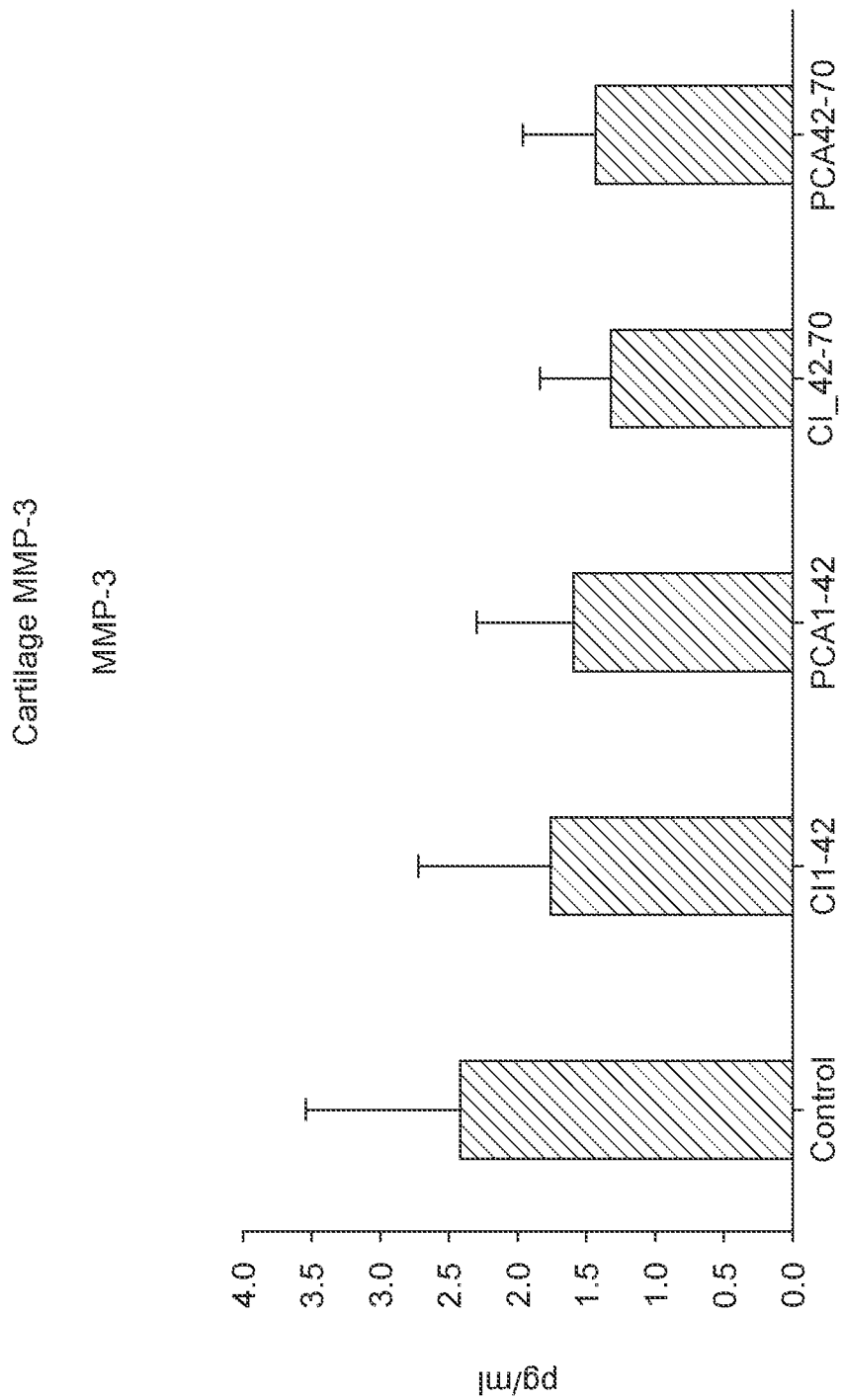
FIG. 3 shows that MMP-3 expression in cartilage was reduced in the both the therapeutic and the prophylactic G3G and PCA groups.
Figure 4:
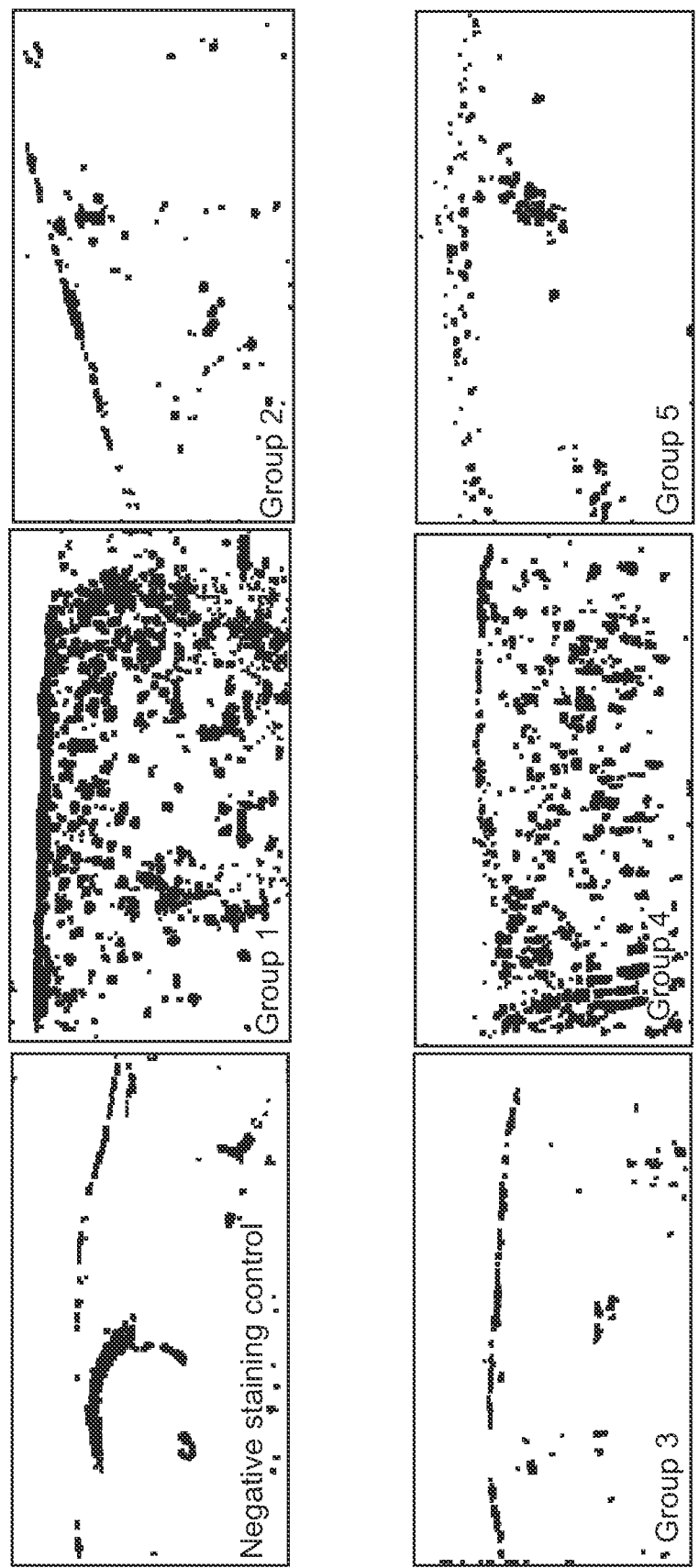
FIG. 4 provides results of histochemical staining for the presence of MMP-3 and expression in cartilage. The negative control shows no staining. Group 1 is a positive control. Group 2 (C3G prophylactic) shows very minimal positive stain for MMP3 with a single arrow pointing to the positive stain. Groups 3 (PCA prophylactic) and Group 4 (C3G therapeutic) and Group 5 (PCA therapeutic) show no staining.

MMP-3 expression in cartilage was reduced in the both the therapeutic and the prophylactic G3G and PCA groups. See FIGS. 3 and 4.

IGF-1

Insulin-like growth factor 1 (IGF-1), also called somatomedin C, is a protein plays an important role in childhood growth and continues to have anabolic effects in adults. Its primary action is mediated by binding to its specific receptor, the insulin-like growth factor 1 receptor (IGF1R), which is present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the anterior pituitary gland, is released into the blood stream, and then stimulates the liver to produce IGF-1. IGF-1 then stimulates systemic body growth, and has growth-promoting effects on almost every cell in the body, especially skeletal muscle, cartilage, bone, liver, kidney, nerves, skin, hematopoietic cell, and lungs.

IGF-1 was increased in the plasma only in the prophylactic PCA group as measured by PG/ML.

Figure 5A:
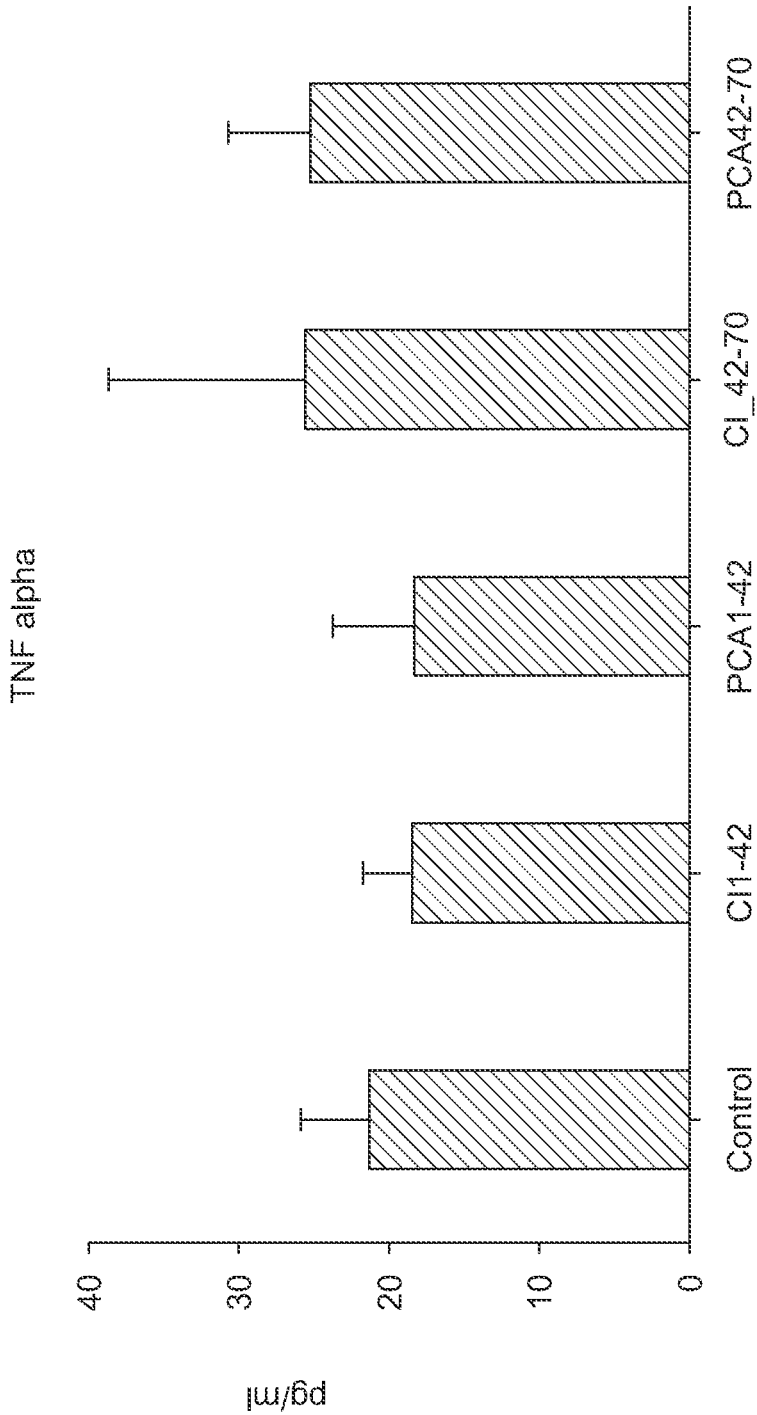
FIG. 5A shows that TNF-alpha levels showed a slight increase in the synovial fluid for the C3G and PCA therapeutic groups and a slight decrease in both of the therapeutic groups. However, the differences seen are not statistically significant. However, notably the reduction occurred due to the longer treatment time; 6 weeks in the prophylactic group as opposed to 4 weeks in the therapeutic groups. Thus, a viable therapy would preferably have a minimum 6-week duration required for depression of TNF-$\alpha$.
Figure 5B:
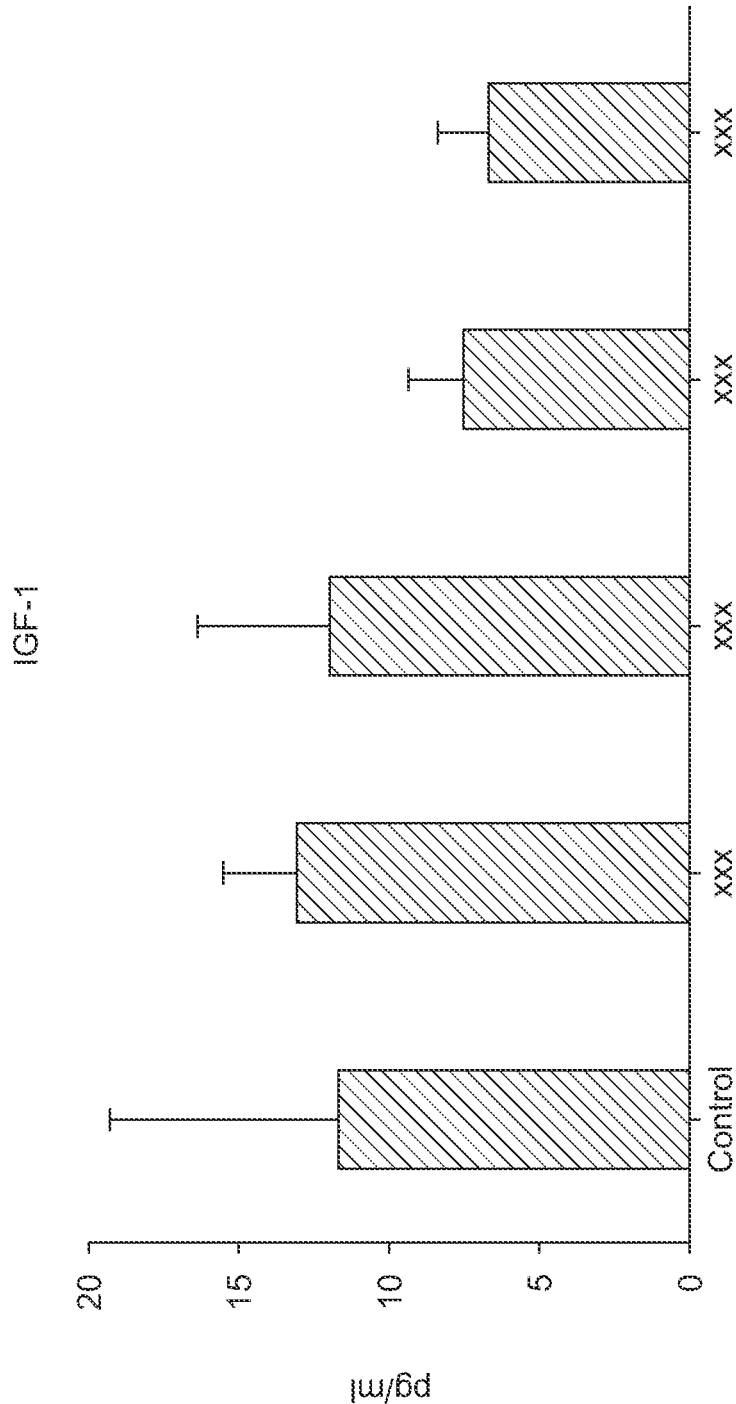
FIG. 5B shows that IFG-1 levels in the synovial fluid was not significantly changed in all groups. However, notably the levels were slightly elevated in the 6-week prophylactic group, but not the 4 week therapeutic groups. This may hint that the timing of the treatment may be important. Further the results shown in this graph also has to be balanced by the synovial fluid IGF-1 receptor amounts detected by ELISA. IGF-1 was active in preserving the patellar cartilage.
Figure 8A:
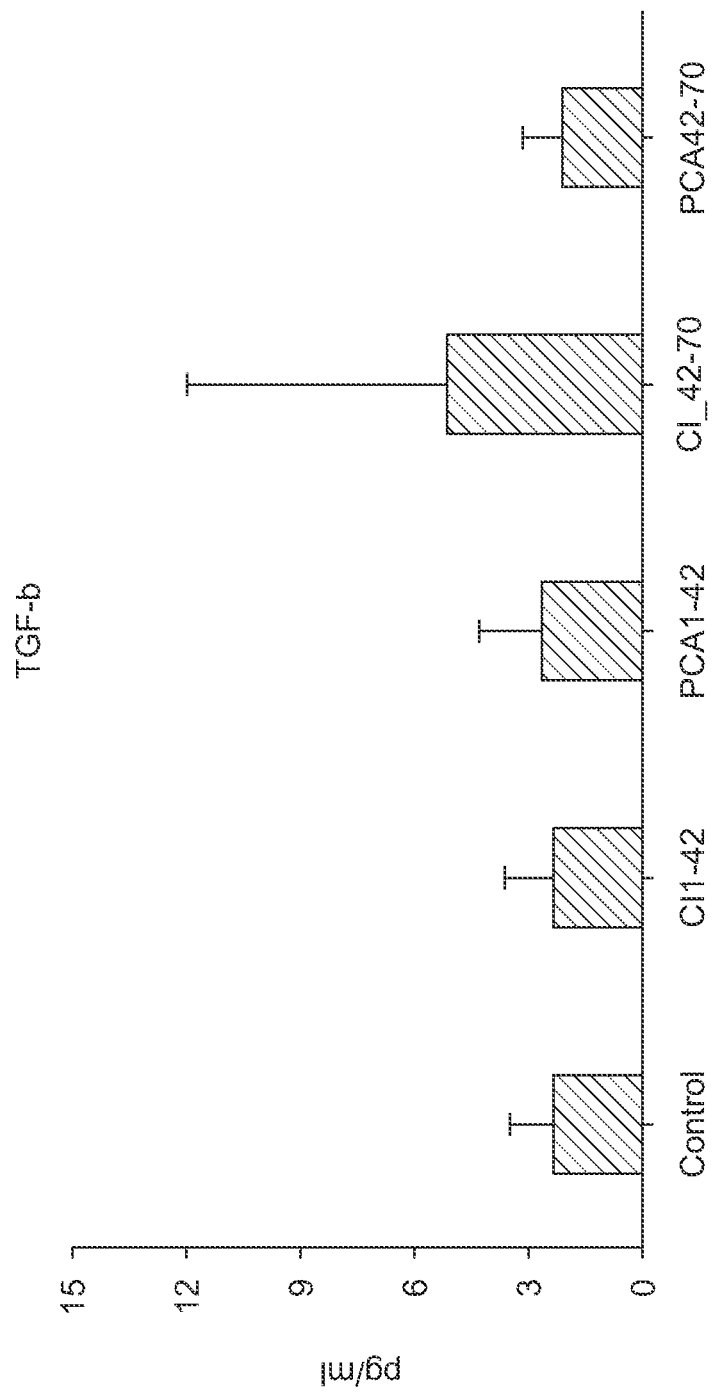
FIG. 8A shows that TGF-beta was increased in the synovium only in the C3G therapeutic group.
Figure 8B:
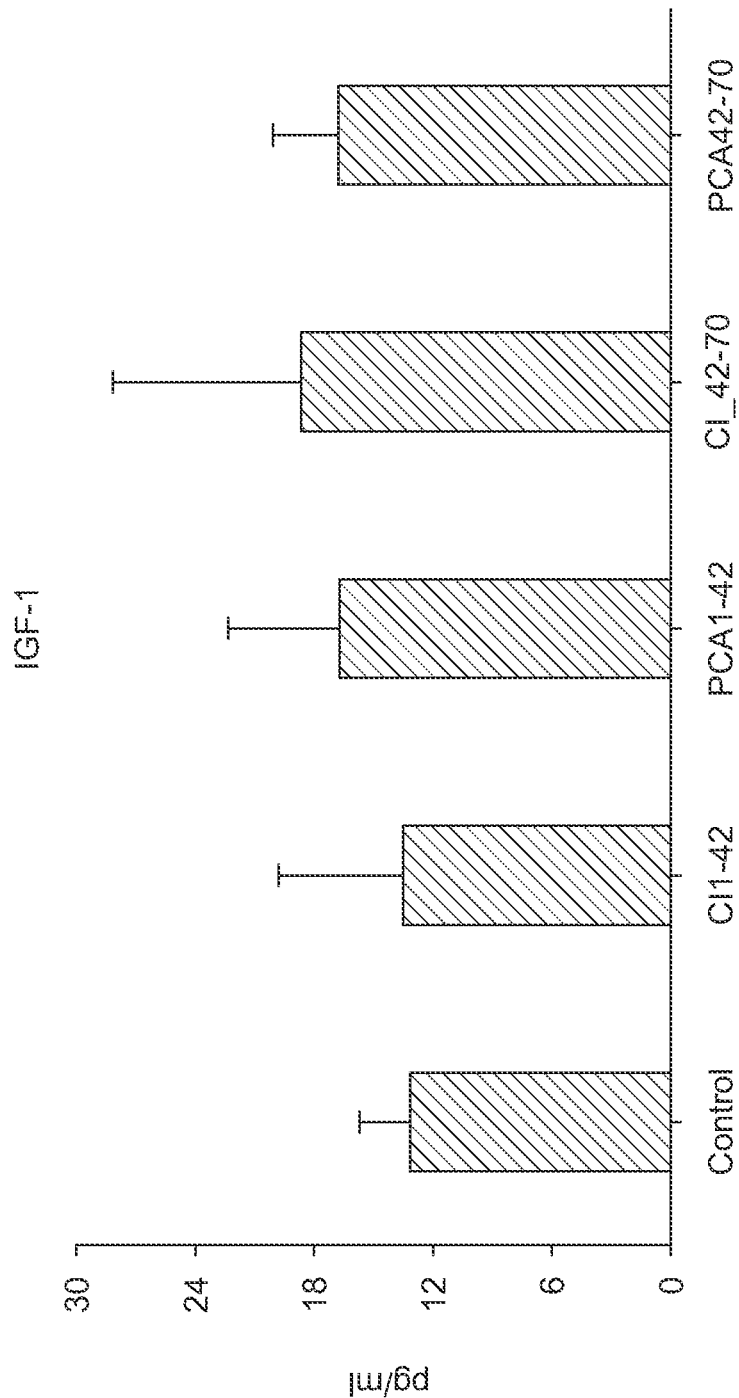
FIG. 8B shows that IGF-1 levels in the synovium was increased in all groups.
Figure 13B:
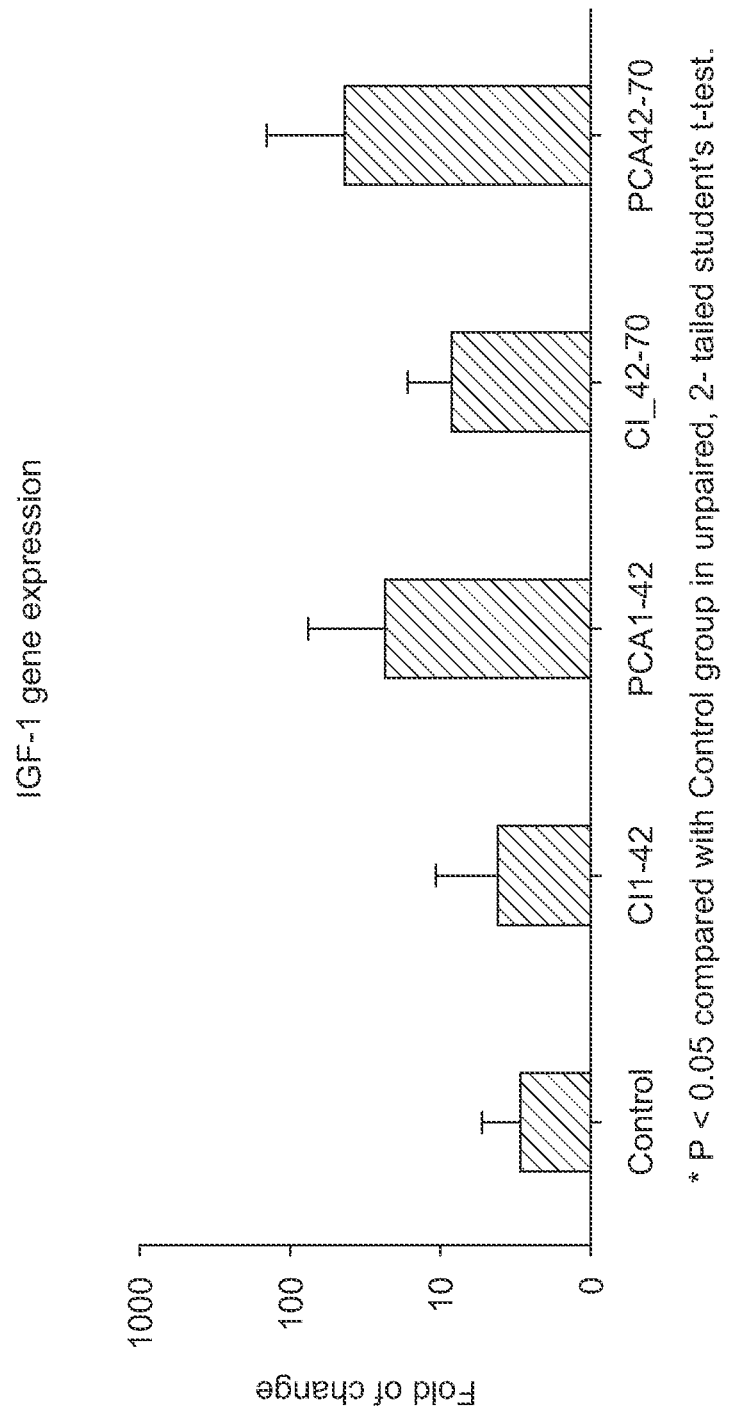
FIG. 13B shows that IGF-1 gene expression as detected by real-time PCR was increased in all groups.

Control group: 25 PG/ML
Prophylactic C3G group: 15.8 PG/ML
Prophylactic PCA group: 43.0 PG/ML
Therapeutic C3G group: 28.5 PG/ML
Therapeutic PCA group: 29.0 PG/ML
Synovial Fluid-Detected by ELISA
IFG-1 was not statistically significantly changed in all groups. See FIG. 5B.
Synovial Tissue (Synovium)-Detected by ELISA
IGF-1 was increased in all groups. See FIG. 8B.
Synovial Tissue (Synovium)-Gene Expression Level Detected by Real-Time PCR
IGF-1 was increased in all groups. See FIG. 13B.
MMP-1

Matrix metalloproteinase-1 (MMP-1) also known as interstitial collagenase and fibroblast collagenase is an enzyme that is involved in the breakdown of extracellular matrix in normal physiological processes, such as embryonic development, reproduction, and tissue remodeling, as well as in disease processes, such as arthritis and metastasis. Specifically, MMP-1 breaks down the interstitial collagens, types I, II, and Ill.

Figure 7:
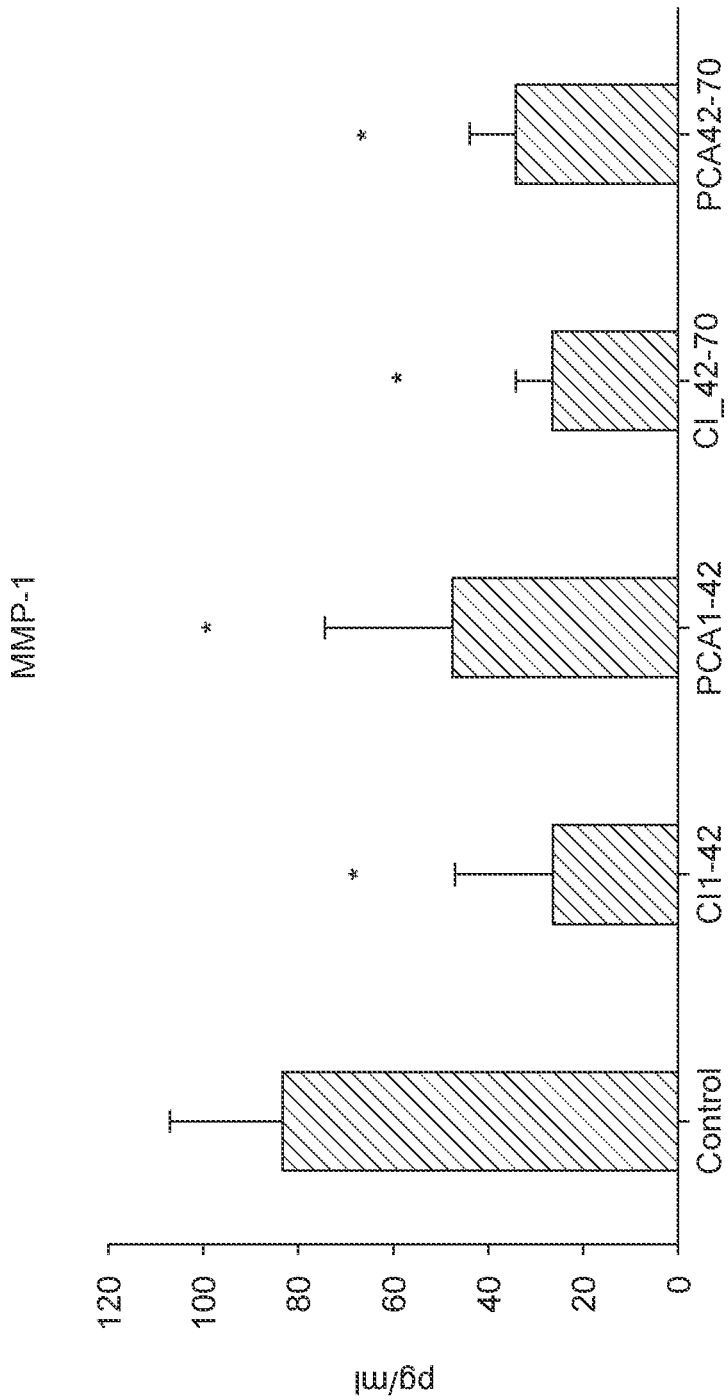
FIG. 7 shows that MMP-I levels in the synovial fluid were decreased significantly in all groups.
Figure 11:
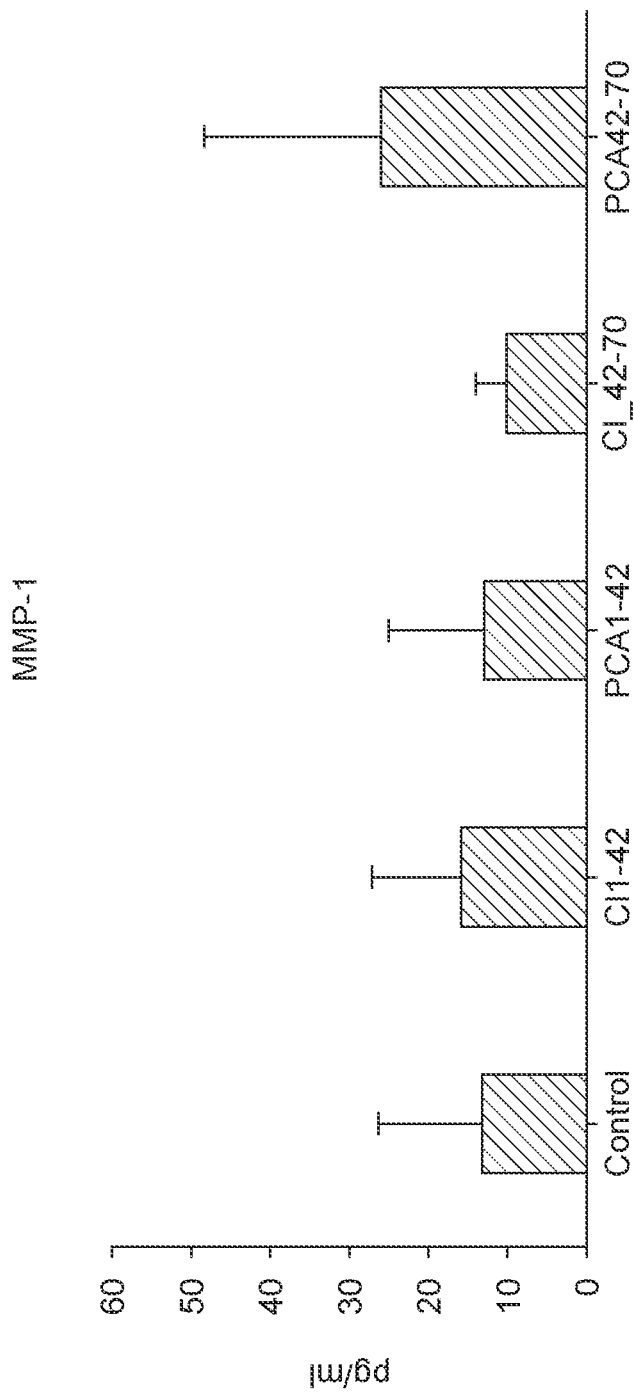
FIG. 11 shows that the therapeutic C3G group showed a decrease in MMP-1 in the synovium.

Synovial Fluid-Detected by ELISA
MMP-1 was decreased significantly in all groups. See FIG. 7.
Synovial Tissue (Synovium)-Detected by ELISA
The therapeutic C3G group showed a decrease in MMP-1 in the synovium. See FIG. 11.
II-1 Beta Interleukin-1 beta (IL-1p) also known as catabolic, is a cytokine protein. This cytokine is an important mediator of the inflammatory response, and is involved in a variety of cellular activities, including cell proliferation, differentiation, and apoptosis. Increased production of IL-1B causes a number of different auto-inflammatory syndromes.

Figure 14:
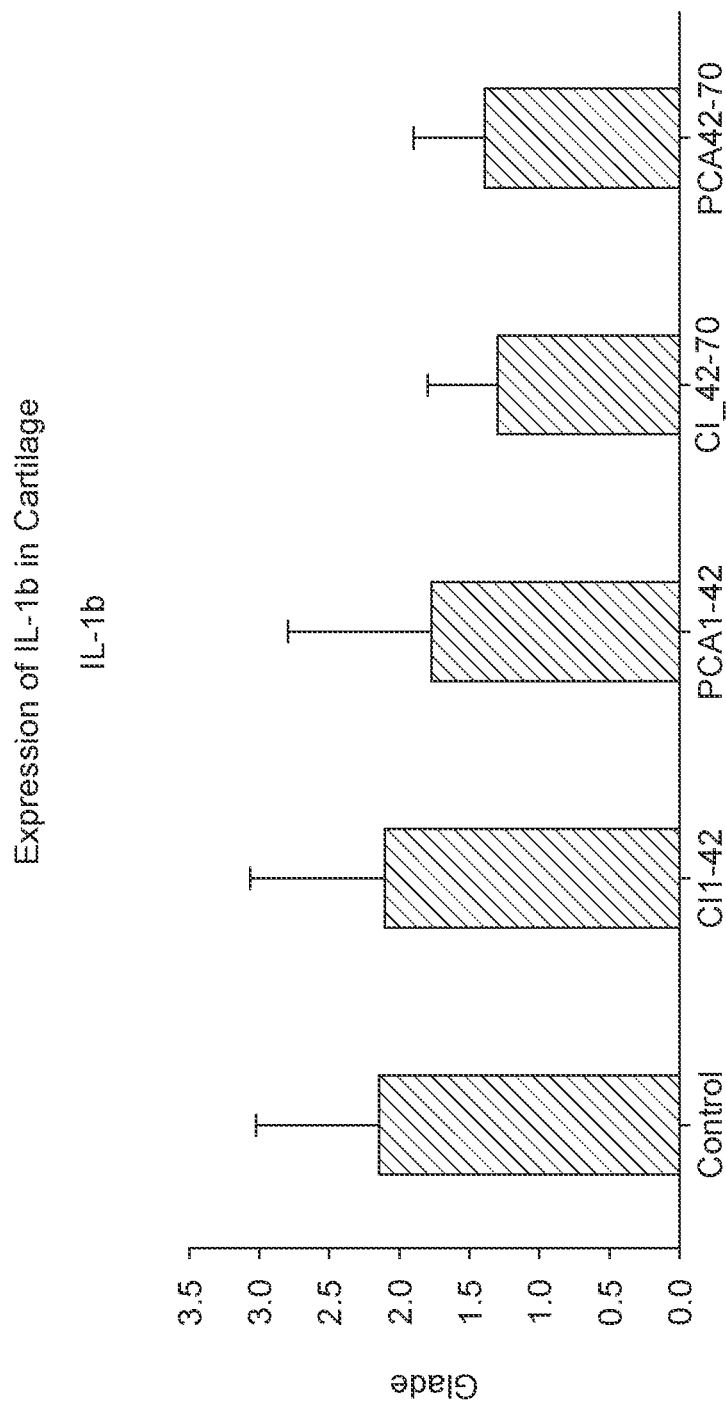
FIG. 14 shows that expression of IL-Beta in cartilage is decreased in all four groups.
Figure 15:
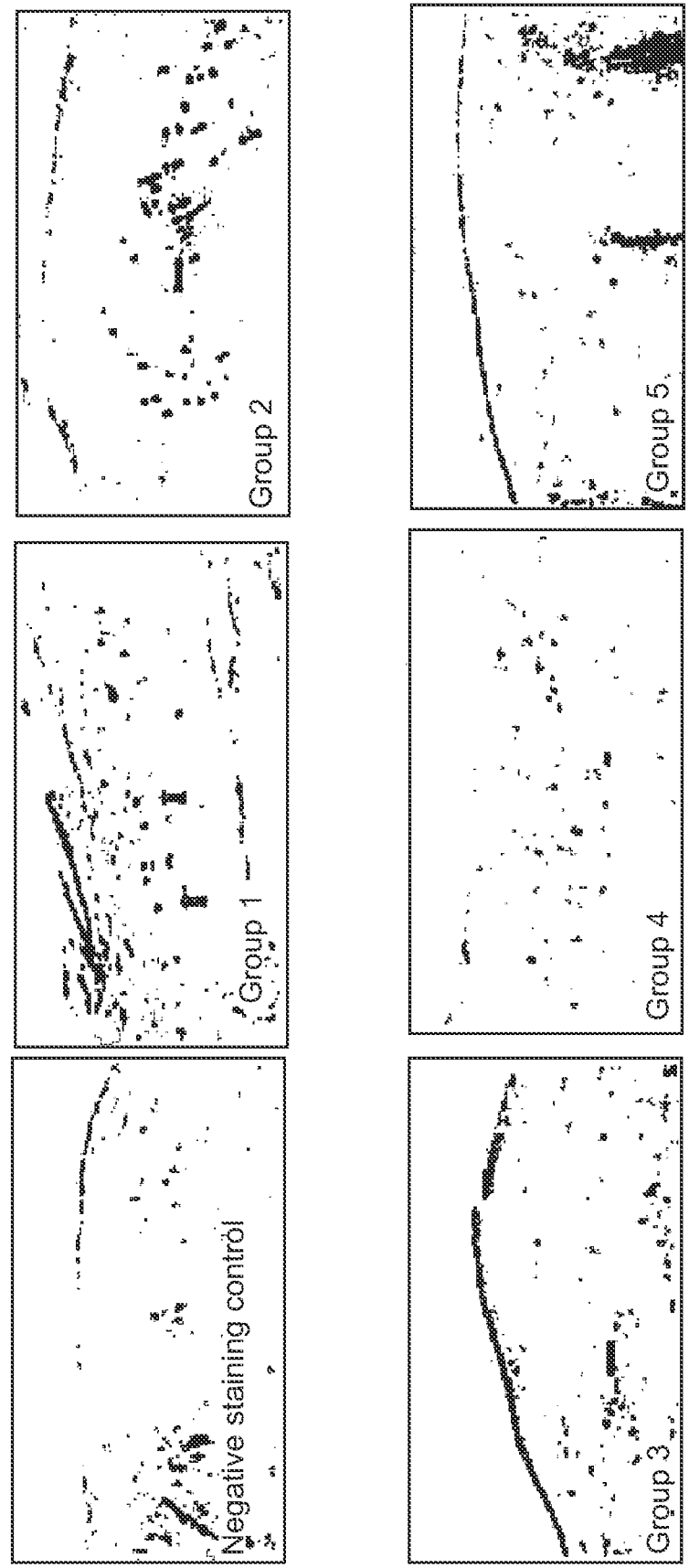
FIG. 15 shows the results of immunohistochemical staining for IL-Beta in rabbit tissue supporting FIG. 14.

Synovial Fluid—Detected by ELISA
Levels of IL-1 beta were decreased in all groups. See FIG. 2A.
Synovial Tissue (Synovium)—Detected by ELISA
Levels of IL-1 beta were decreased in the C3G and PCA therapeutic groups but were increased in the two prophylactic groups. See FIG. 9A.
Expression in Cartilage
FIGS. 14 and 15 show that expression of IL-Beta in cartilage is decreased in all four groups.
TGF-beta TGF-β induces apoptosis in numerous cell types. Transforming growth factor beta (TGF-β) is a protein that controls proliferation, cellular differentiation, and other functions in most cells. It is a type of cytokine which plays a role in immunity, cancer, bronchial asthma, heart disease, diabetes, hereditary hemorrhagic telangiectasia, Marfan syndrome, vascular Ehlers-Danlos syndrome Loeys-Dietz syndrome, Parkinson's disease, and AIDS.

Synovial Fluid—Detected by ELISA
TGF-beta was decreased in all groups. See FIG. 2B.
Synovial Tissue (Synovium)—Detected by ELISA
TGF-beta was increased in the C3G therapeutic group. See FIG. 8A.
Lubricin Proteoglycan 4 or lubricin is a proteoglycan that acts as a joint/boundary lubricant. Lubricin is present in synovial fluid and on the surface (superficial layer) of articular cartilage and therefore plays an important role in joint lubrication and synovial homeostasis.

Exposure of synoviocytes, chondrocytes and cartilage explants to proinflammatory cytokines such as II-1 and TNF-alpha results in a marked reduction in the expression and/or abundance of secreted lubricin, with corresponding alterations in the amounts of cartilage-associated lubricin. Jones A R C, et al., European Cells and Materials Vol. 13, 2007 (pages 40-45) 2007.

Studies have shown that IL-1 inhibits the presence of lubricin and IGF-1 increases it synthesis. Flannery, C R, et al., Biochemical and Biophysical Research Communications. Vol. 254, Issue 3, 27 Jan. 1999, pages 535-541.

Figure 8C:
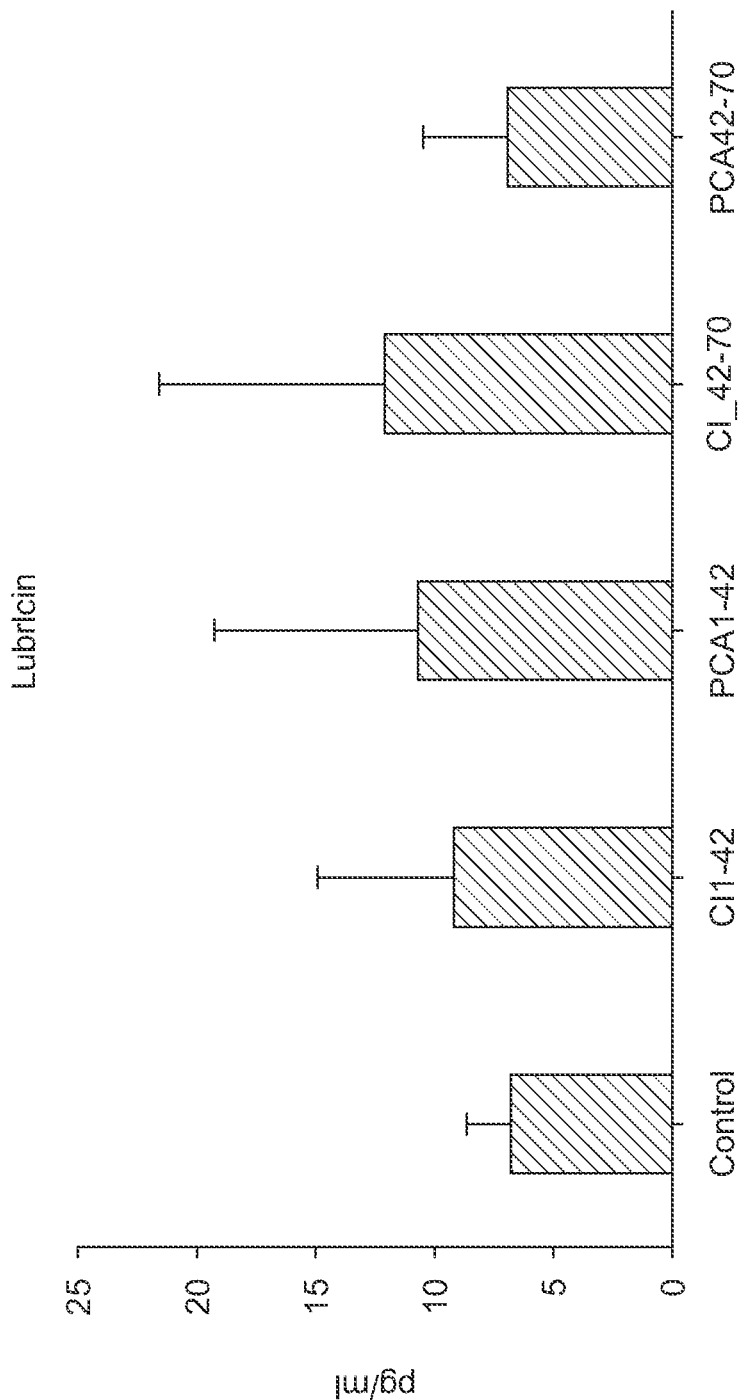
FIG. 8C shows that lubricin was increased in 3 of the 4 groups in the synovium (increase in both C3G groups and increase in the prophylactic PCA group).
Figure 18:
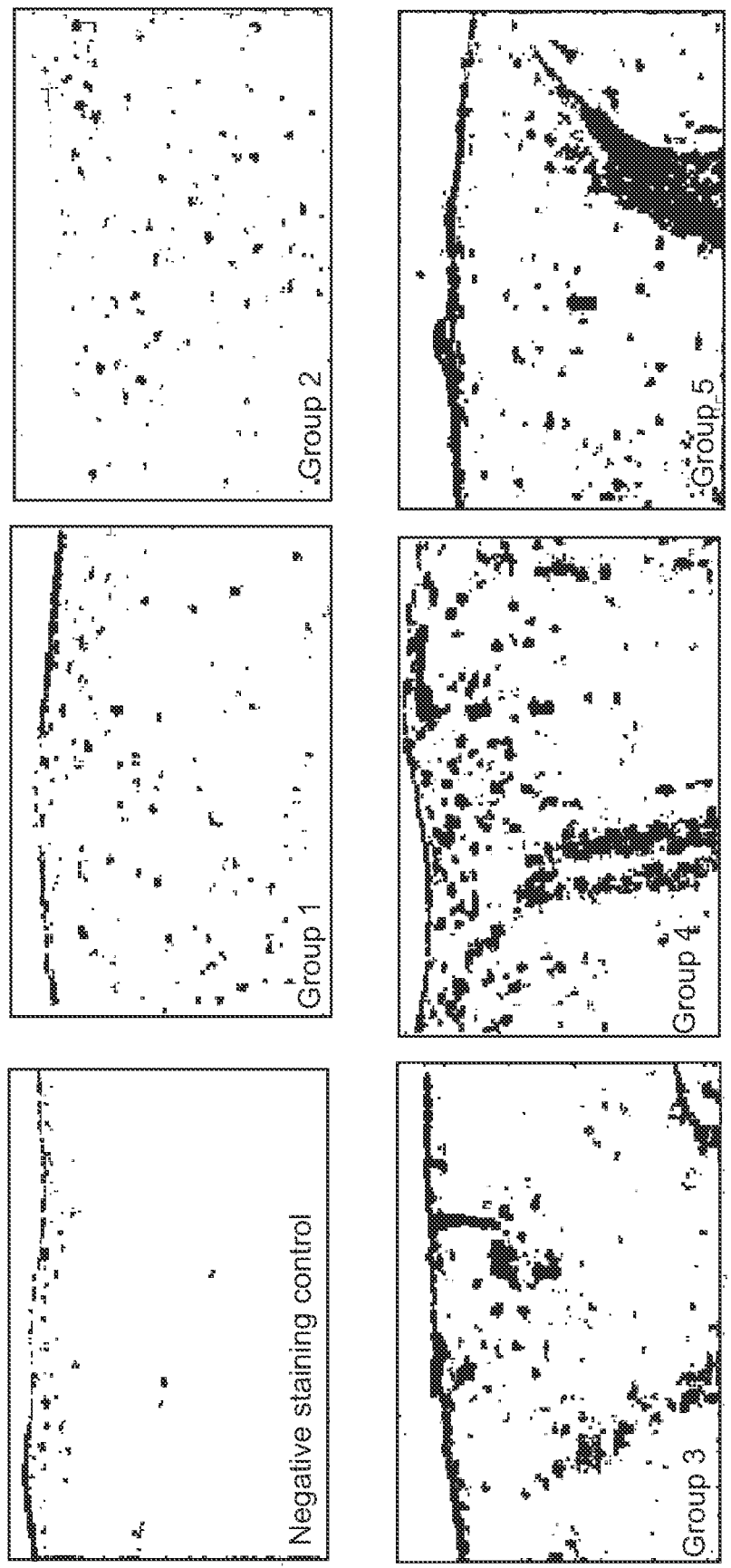
FIG. 18 provides the underlying immunohistochemical staining supporting FIG. 19.
Figure 19:
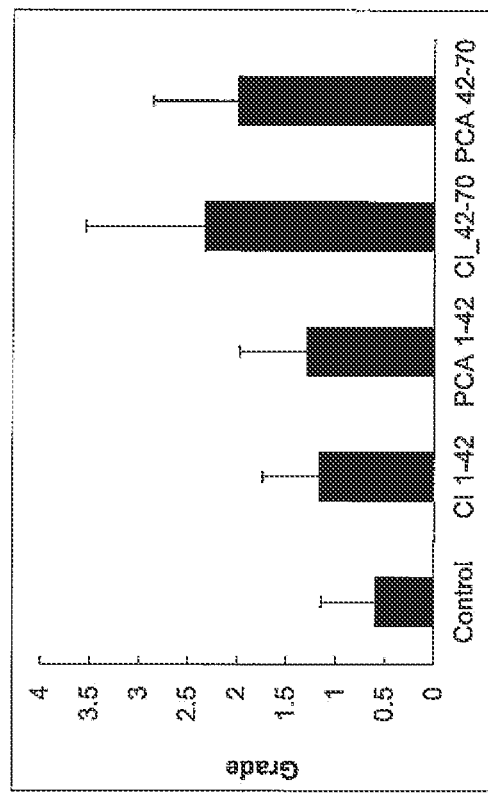
FIG. 19 shows that lubricin expression was increased in the cartilage of all four groups.

Synovial Tissue (Synovium)—Detected by ELISA
Lubricin was increased in 3 of the 4 groups in the synovium (increase in both C3G groups and increase in the prophylactic PCA group). (See FIG. 8C).
Expression in Cartilage
FIGS. 18 and 19 show that lubricin expression was increased in the cartilage of all four groups.
II-6

Interleukin 6 (IL-6) is an interleukin that acts as both a pro-inflammatory cytokine and an anti-inflammatory myokine. IL-6 is secreted by T cells and macrophages to stimulate immune response, e.g. during infection and after trauma, especially burns or other tissue damage leading to inflammation. In addition, osteoblasts secrete IL-6 to stimulate osteoclast formation. IL-6's role as an anti-inflammatory cytokine is mediated through its inhibitory effects on TNF-alpha and IL-1, and activation of IL-1ra and IL-10. IL-6 is an important mediator of fever and of the acute phase response.

Figure 9C:
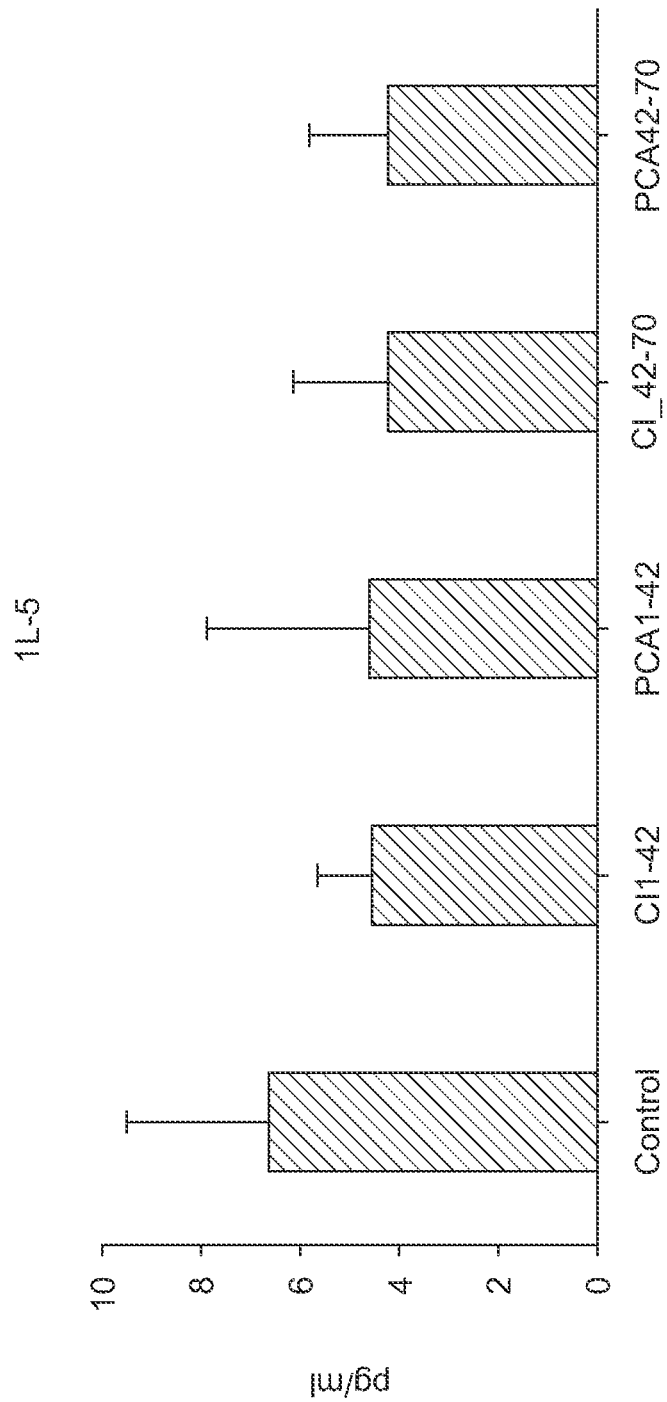
FIG. 9C shows that IL-6 was decreased in the synovium in all groups.

Synovial Tissue (Synovium)—Detected by ELISA
11-6 was decreased in all groups. See FIG. 9C.
TNF-Alpha Tumor necrosis factor (TNF, cachexin, or cachectin, and formerly known as tumor necrosis factor alpha or TNFα) is an adipokine involved in systemic inflammation and is a member of a group of cytokines that stimulate the acute phase reaction. It is produced chiefly by activated macrophages, although it can be produced by many other cell types such as CD4+ lymphocytes, NK cells, neutrophils, mast cells, eosinophils, and neurons. The primary role of TNF is in the regulation of immune cells. TNF, being an endogenous pyrogen, is able to induce fever, apoptotic cell death, cachexia, inflammation and to inhibit tumorigenesis and viral replication and respond to sepsis via IL1 and IL6 producing cells.

TNF promotes the inflammatory response, which, in turn, causes many of the clinical problems associated with autoimmune disorders such as rheumatoid arthritis, ankylosing spondylitis, inflammatory bowel disease, psoriasis, hidradenitis suppurativa and refractory asthma.

TNF and II-1 are considered master cytokines in chronic, destructive arthritis. In fact, therapeutic approaches to rheumatoid arthritis (RA) is mainly focuses on TNF. Analysis of cytokine patterns in early synovial biopsy specimens of RA patients reveals prominent TNF staining in 50% of the patients, whereas IL-1beta staining was evident in 100% of the patients. Van den Berg W B., Ann Rheum Dis., November 2000; 59 (Supp 1); i81-i84.

Synovial Fluid—Detected by ELISA

TNF-alpha levels showed a slight decrease in both of the prophylactic groups. See FIG. 5A.

Synovial Tissue (Synovium)-Detected by ELISA

Figure 9D:
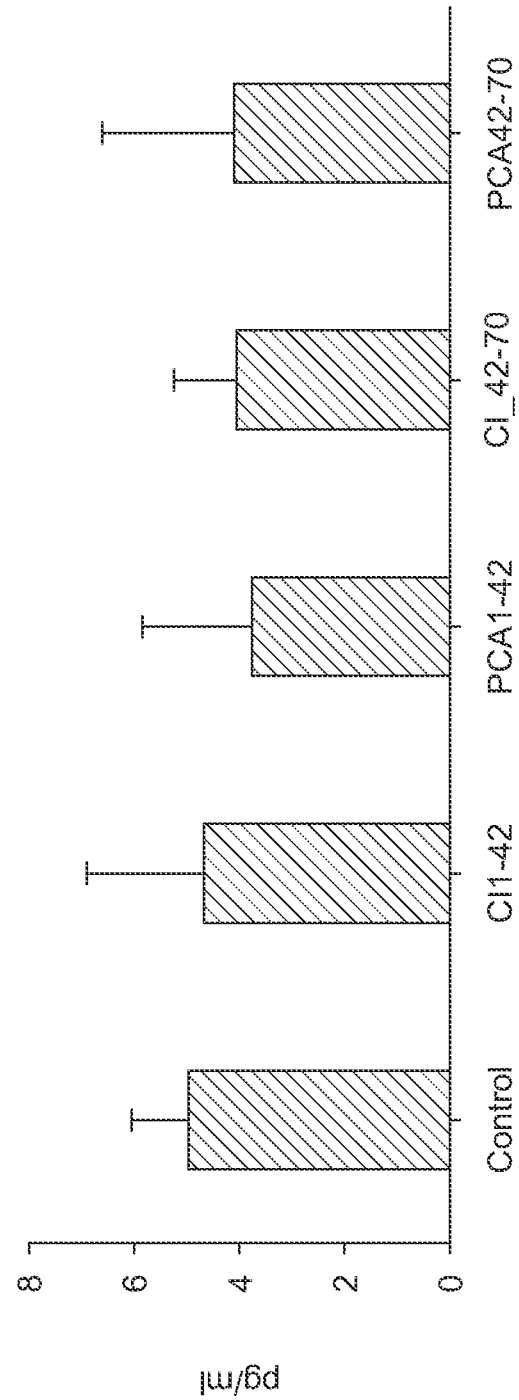
FIG. 9D shows that TNF-alpha levels were decreased in the synovium for all groups.

TNF-alpha levels were decreased in all groups. See FIG. 9D.

ADAMTS-5

ADAMTS-5 is a disintegrin and metalloproteinase with thrombospondin motifs. ADAMTS5 is a member of the ADAMTS protein family. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, which is a critical component of cartilage and joints. Thus ADAMTS-5 has a catabolic effect on cartilage.

Synovial Fluid—Detected by ELISA

Figure 6A:
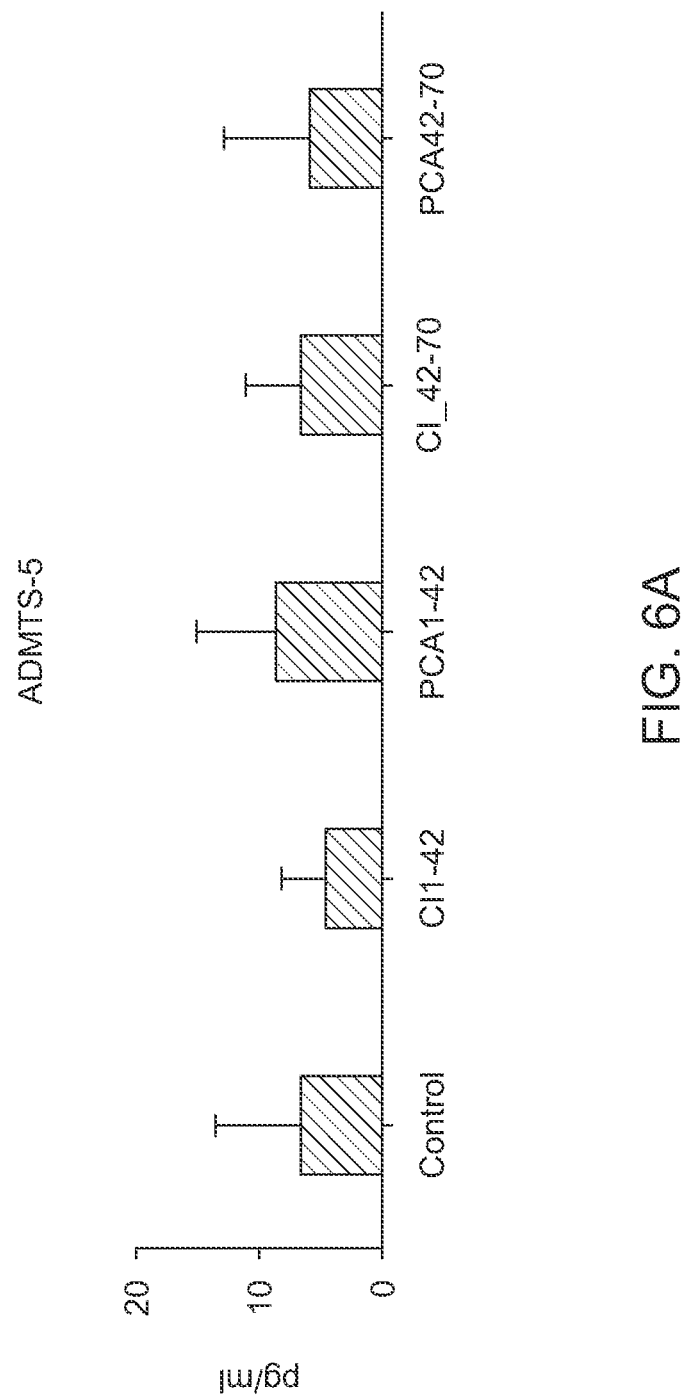
FIG. 6A shows that ADAMTS-5 was decreased in the synovial fluid in both C3G groups and in the therapeutic PCA group.

ADAMTS-5 was decreased in both C3G groups and an in the therapeutic PCA group. See FIG. 6A.

Synovial Tissue (Synovium)—Gene Expression Level Detected by Real-Time PCR

Figure 12:
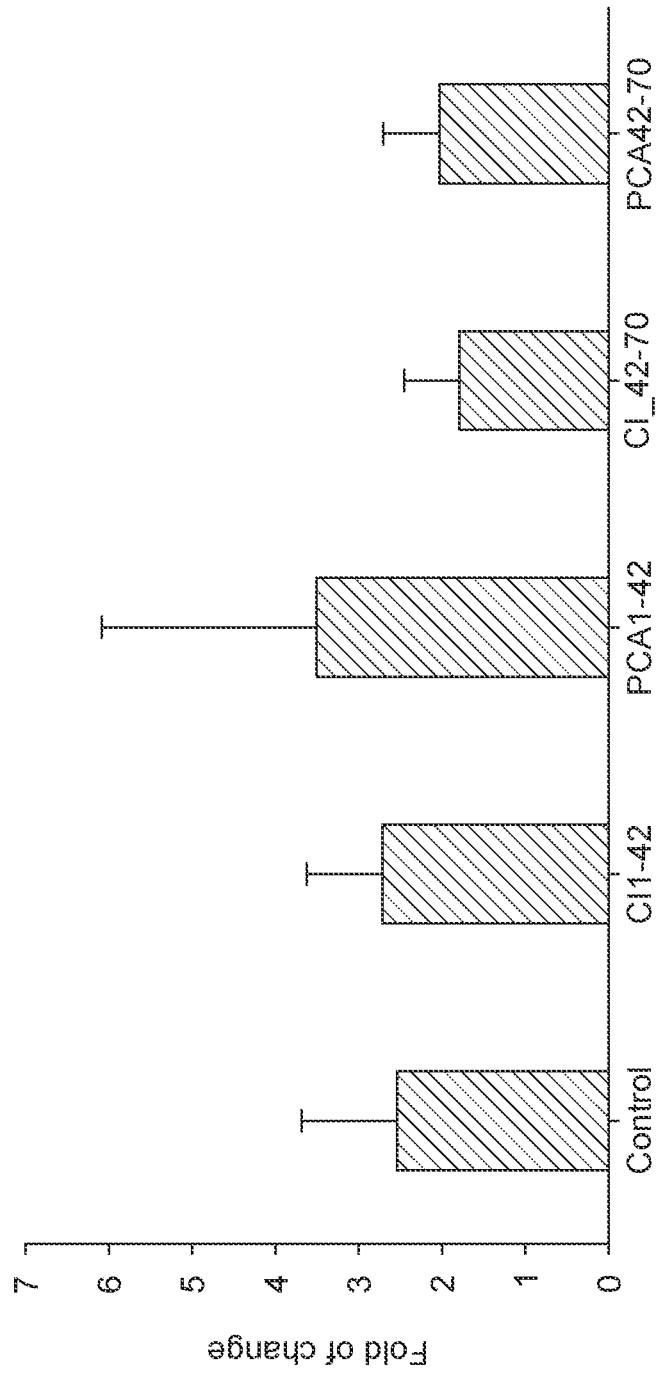
FIG. 12 shows that ADAMTS-5 gene expression was decreased in the synovium in the C3G and the PCA therapeutic groups.

ADAMTS-5 gene expression was decreased in the synovium in the C3G and the PCA therapeutic groups. See FIG. 12.

MMP-13

MMP-13 is also known as collagenase 3 and is an enzyme and a member of the matrix metalloproteinase (MMP) family. During embryonic development, MMP13 is expressed in the skeleton as required for restructuring the collagen matrix for bone mineralization. In pathological situations it is highly overexpressed; this occurs in human carcinomas, rheumatoid arthritis, and osteoarthritis. Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. The protein encoded by this gene cleaves type II collagen more efficiently than types I and Ill. It may be involved in articular cartilage turnover and cartilage pathophysiology associated with osteoarthritis.

Synovial Fluid—Detected by ELISA

Figure 6B:
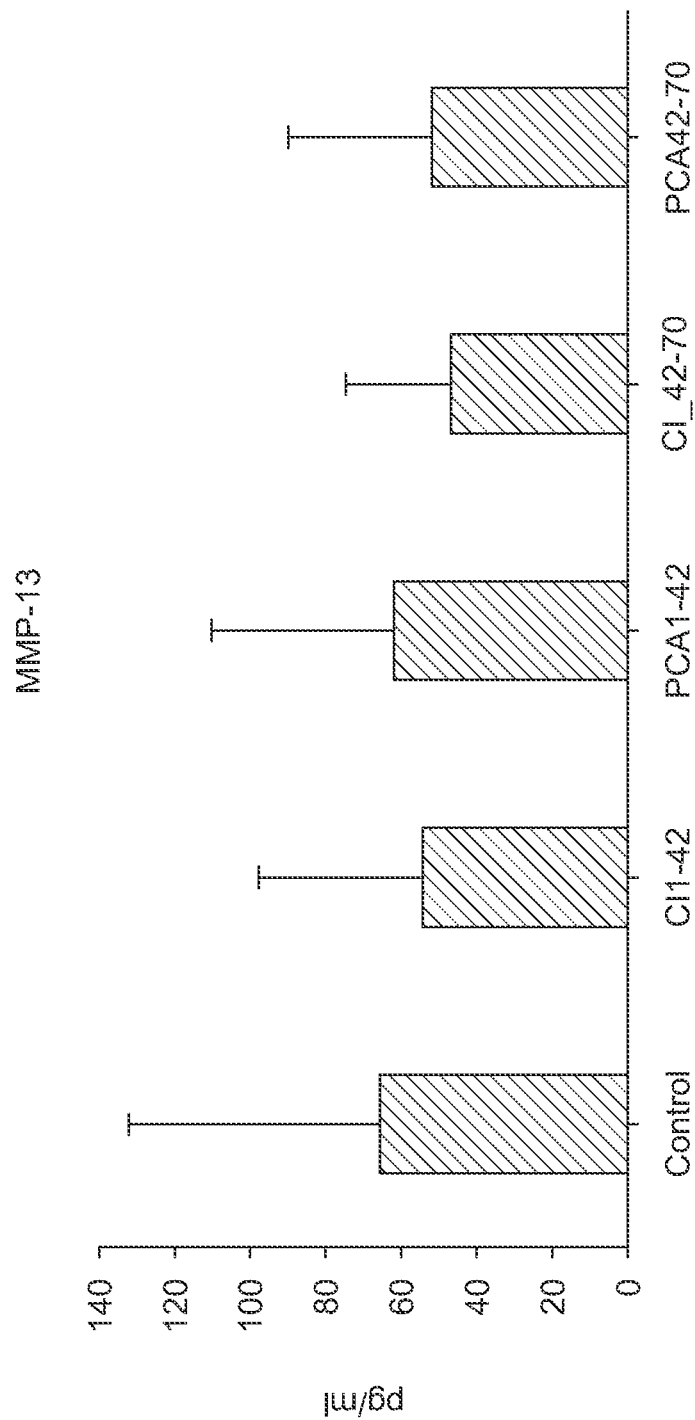
FIG. 6B shows that MMP-13 was decreased in the synovial fluid for all groups.

MMP-13 was decreased in all groups. See FIG. 6B.

Synovial Tissue (Synovium)—Detected by ELISA

MMP-13 levels were slightly decreased in the C3G therapeutic group and very slightly decreased in the PCA prophylactic group. The levels seemed to be increased slightly in the PCA therapeutic and the C3G prophylactic group, but this is not a statistical significant change. See FIG. 1.

TIMP-1

TIMP metallopeptidase inhibitor 1, also known as TIMP1, and is a tissue inhibitor of metalloproteinases. It is a glycoprotein that is expressed from the several tissues of organisms. This glycoprotein is a natural inhibitor of the matrix metalloproteinases (MMPs), a group of peptidases involved in degradation of the extracellular matrix. In addition to its inhibitory role against most of the known MMPs, the encoded protein is able to promote cell proliferation in a wide range of cell types and may also have an anti-apoptotic function.

Synovial Fluid—Detected by ELISA

Figure 6C:
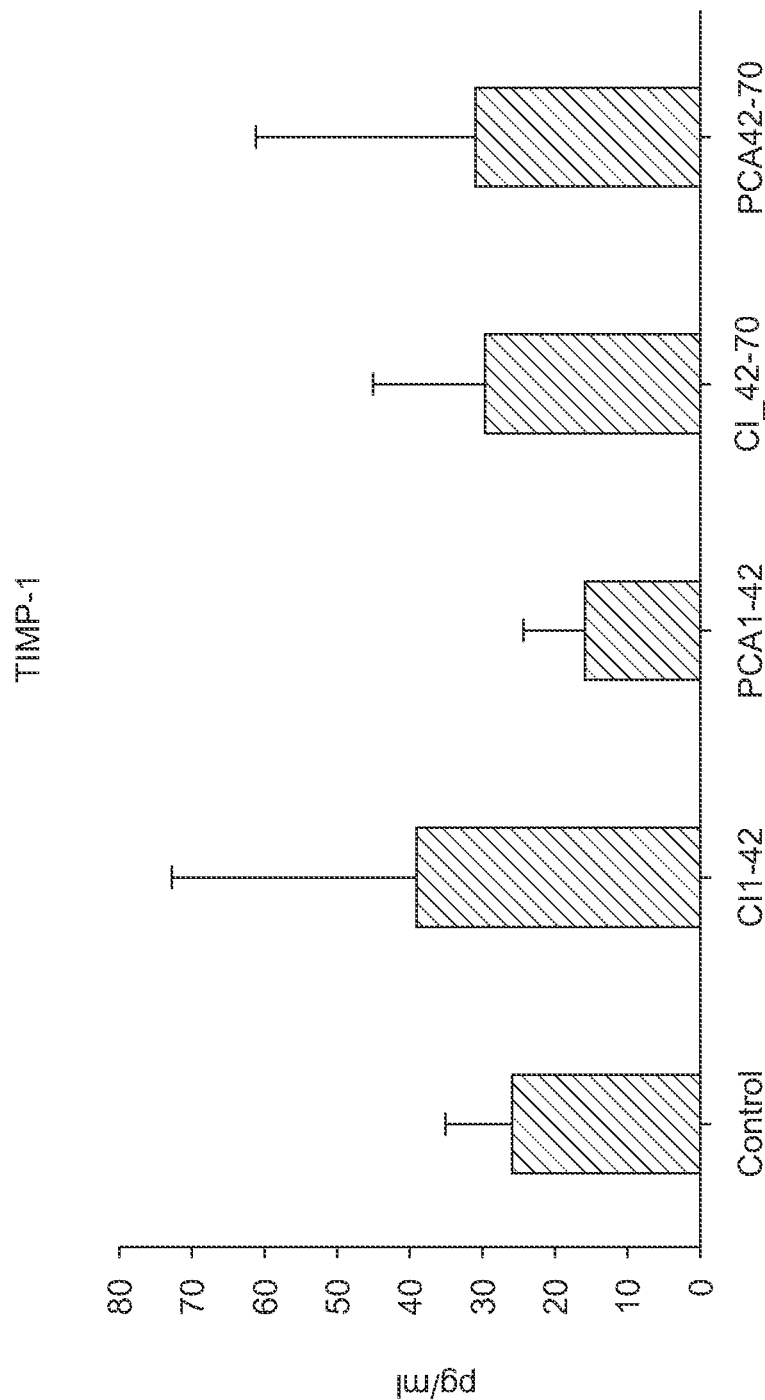
FIG. 6C shows that the TIMP-1 levels were elevated in both C3G groups and lowered in the PCA therapeutic group. However, statistical significance was not evident.

The levels were elevated in both C3G groups and in the PCA therapeutic group. See FIG. 6C.

Synovial Tissue (Synovium)—Gene Expression Level Detected by Real-Time PCR

Figure 10:
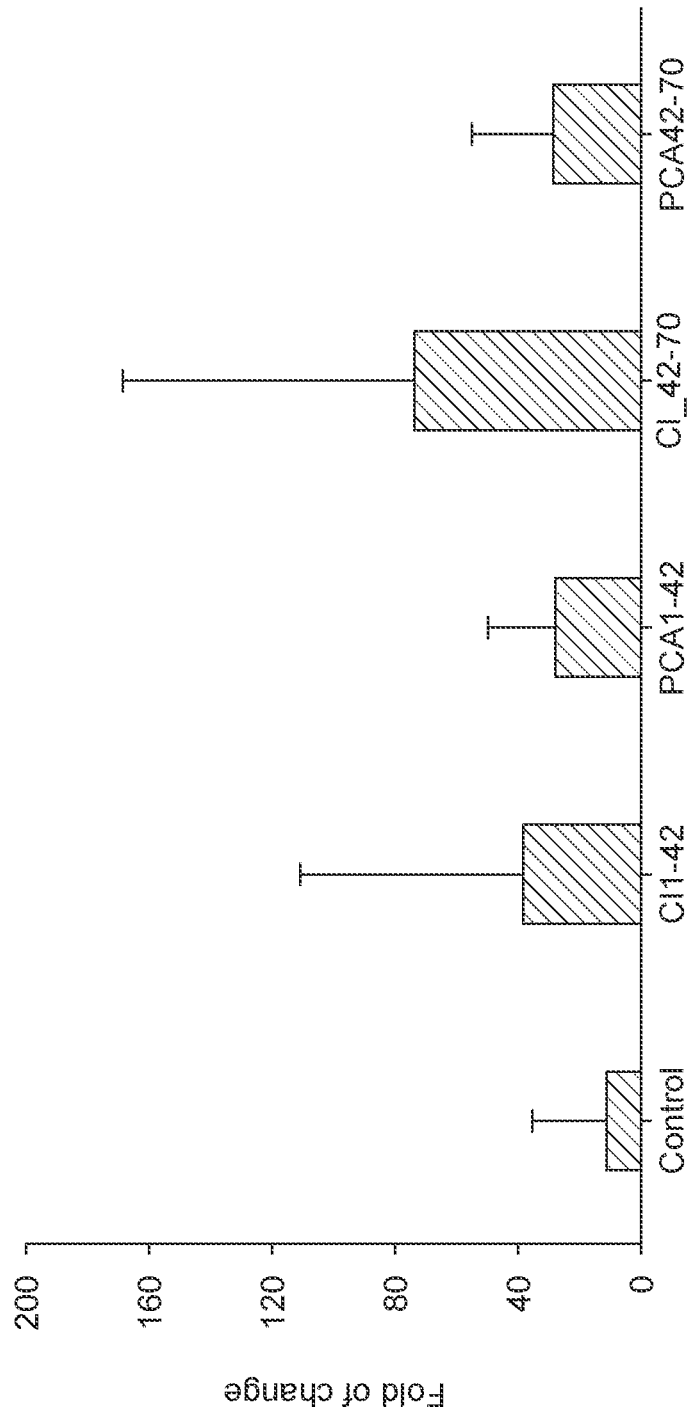
FIG. 10 shows that TIMP-1 gene expression was increased in the synovium in all four test groups.

There was an increase in gene expression in the synovium in all four test groups. See FIG. 10.

VEGF

VEGF is vascular endothelial growth factor that causes neovascularization and stops apoptosis of synovial cells.

Synovium—Detected by ELISA

Figure 27:
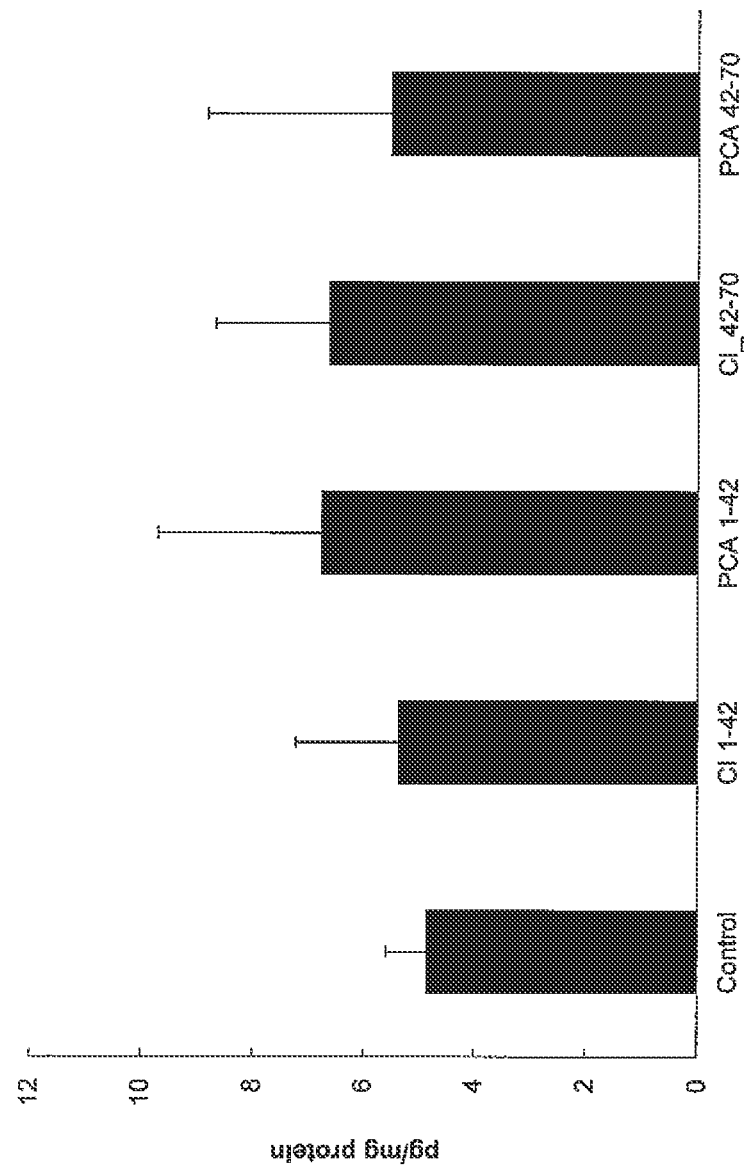
FIG. 27 shows that the levels of VEGF in the synovium were increased in all four groups.

The levels of VEGF were increased in all four groups. See FIG. 27.

IL-10

Interleukin-10 (IL-10), also known as human cytokine synthesis inhibitory factor (CSIF), is an anti-inflammatory cytokine. IL-10 is capable of inhibiting synthesis of pro-inflammatory cytokines such as IFN-γ, IL-2, IL-3, TNFα and GM-CSF made by cells such as macrophages and regulatory T-cells. It also displays a potent ability to suppress the antigen-presentation capacity of antigen presenting cells.

Synovial Fluid—Detected by ELISA

Figure 28:
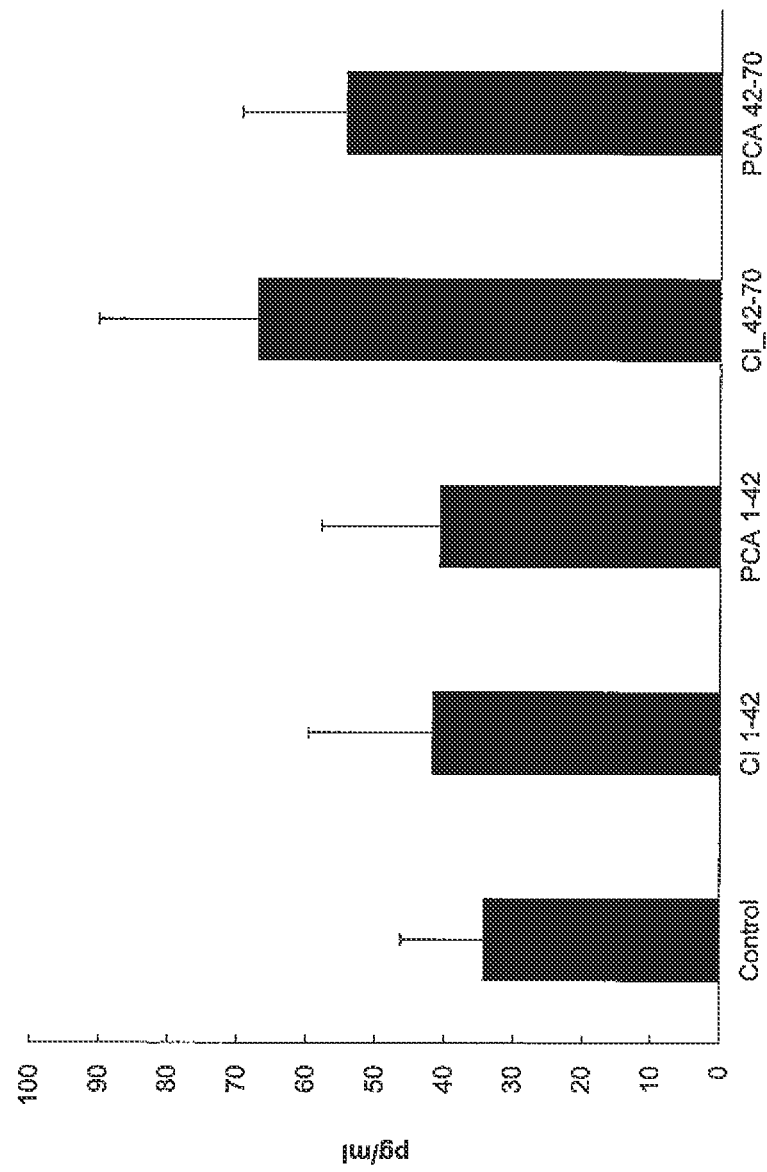
FIG. 28 shows that the levels of IL-10 in the synovial fluid were increased in all four groups.

Levels of IL-10 were increased in all four groups. See FIG. 28.

Il-4

The presence of IL-4 in extravascular tissues promotes alternative activation of macrophages into M2 cells and inhibits classical activation of macrophages into M1 cells. An increase in repair macrophages (M2) is coupled with secretion of IL-10 and TGF-β that result in a diminution of pathological inflammation.

Synovial Fluid—Detected by ELISA

Figure 29:
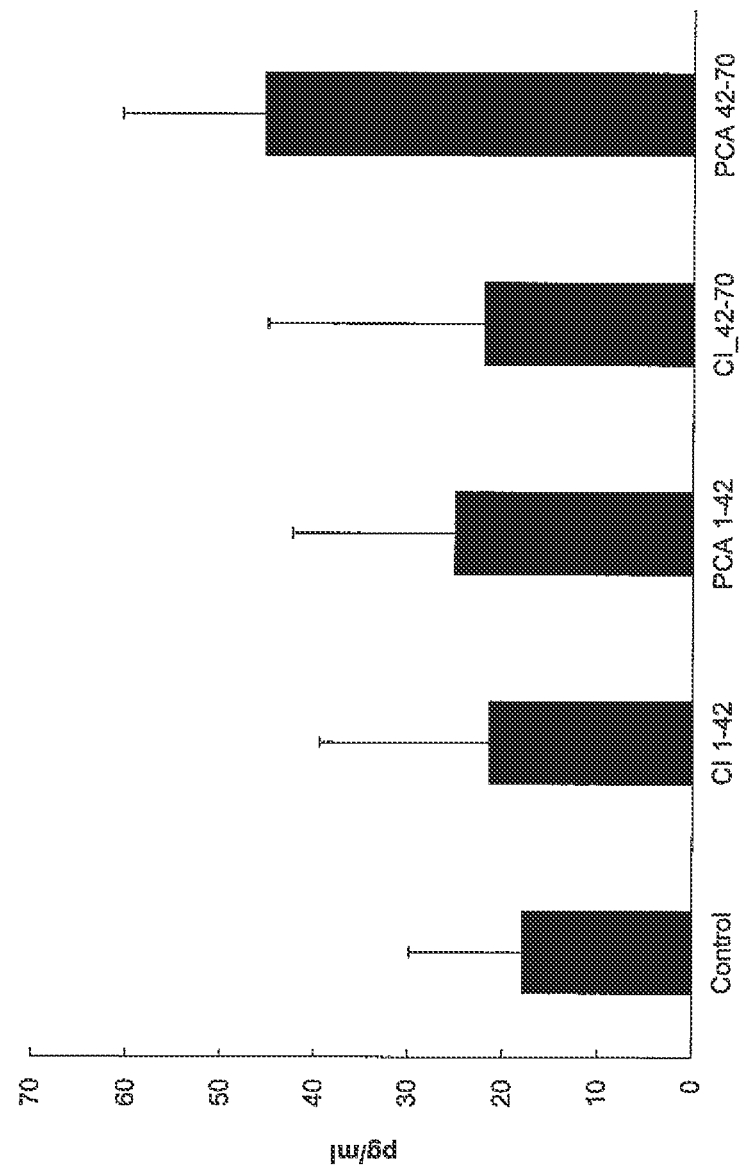
FIG. 29 shows that the levels of IL-4 in the synovial fluid was increased in all four groups.

All four groups showed an increase in IL-4. See FIG. 29.

Collagen II

Collagen II is the bases for articular cartilage and hyaline cartilage. It makes up 50% of all protein in cartilage and 85-905 of the collagen of articular cartilage.

Figure 16:
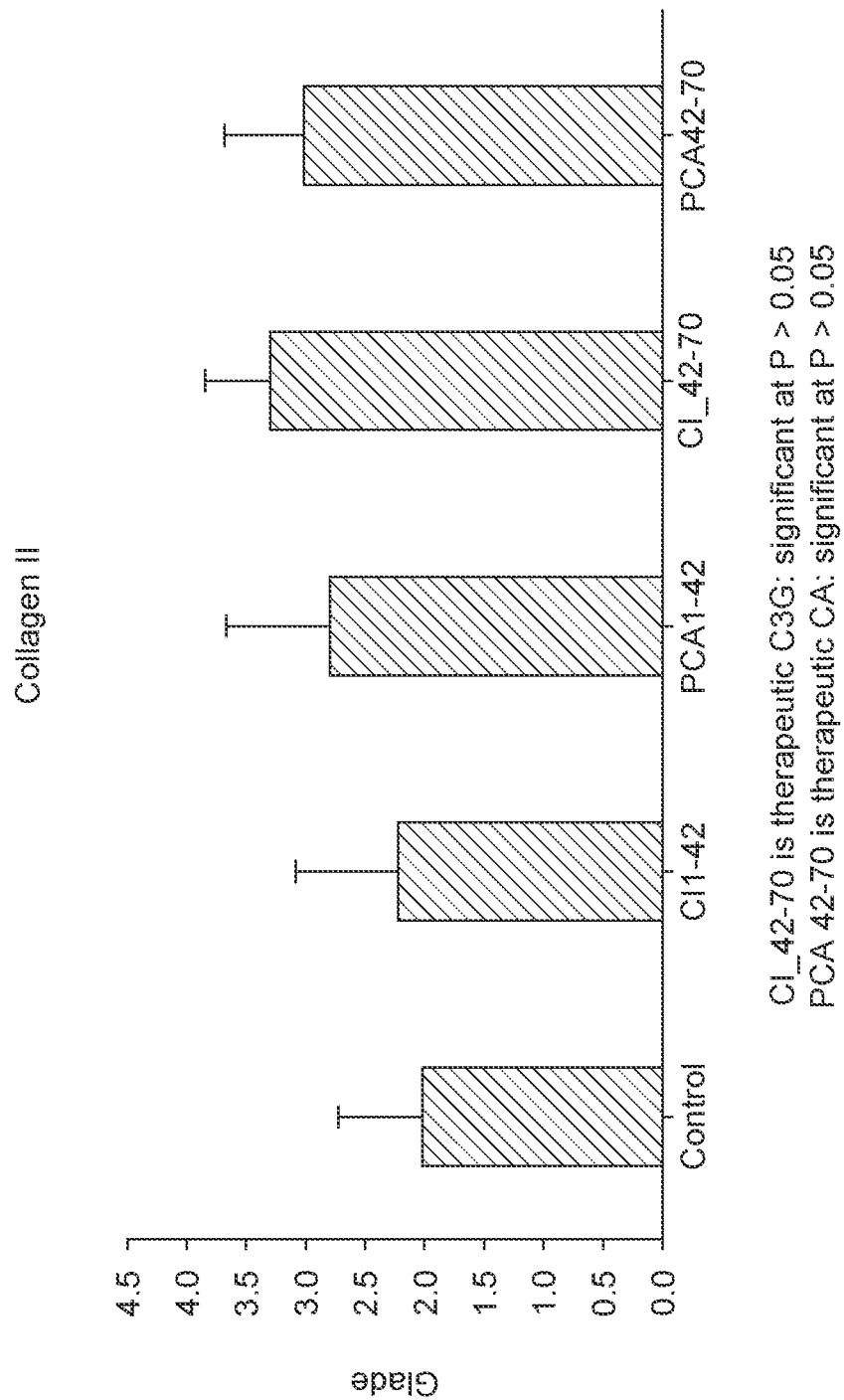
FIG. 16 shows that collagen II expression in cartilage is increased in all4 groups.
Figure 17:
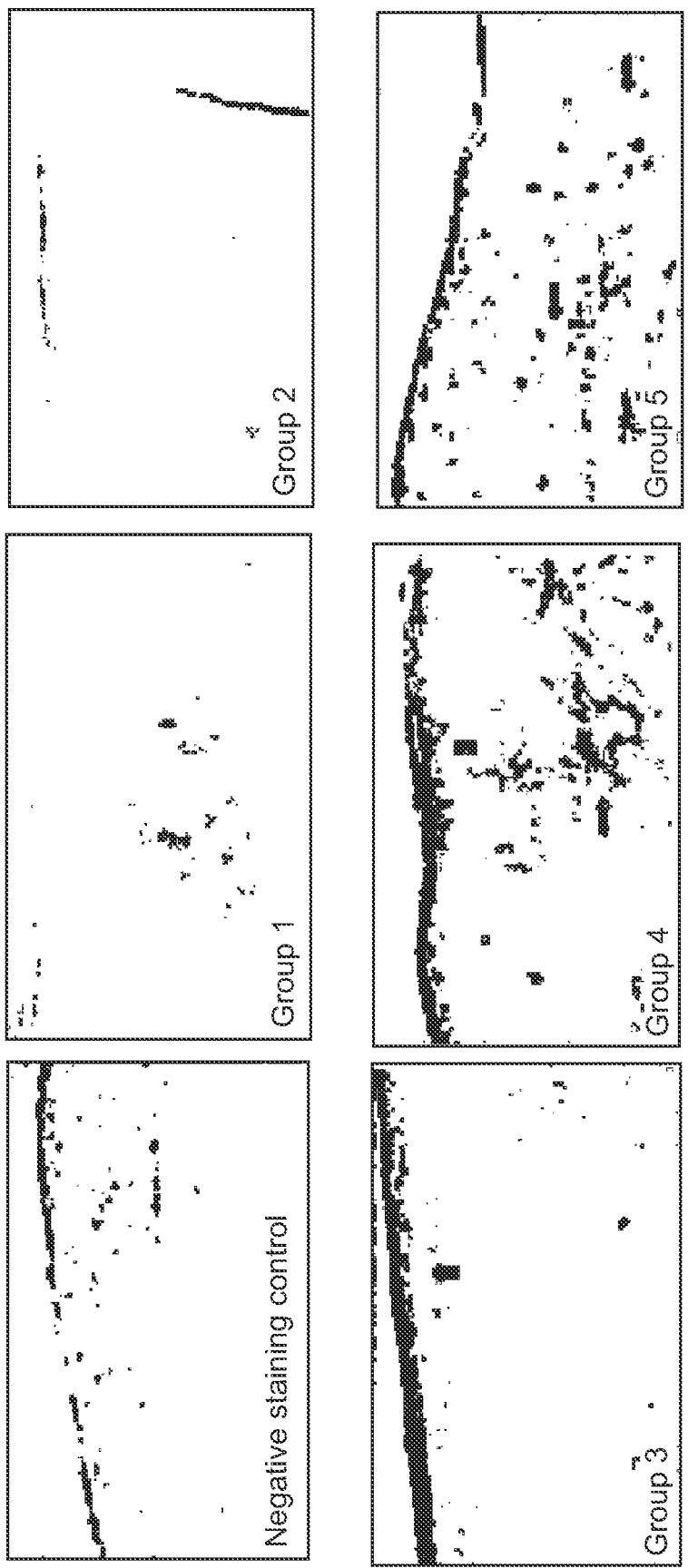
FIG. 17 provides the underlying immunohistochemical staining supporting FIG. 16.

FIGS. 16 and 17 show that collagen II expression in cartilage is increased in all 4 groups.

Aggrecan

Aggrecan is a major component of cartilage extracellular matrix, and it imparts compressive resistance to the tissue.

Figure 20:
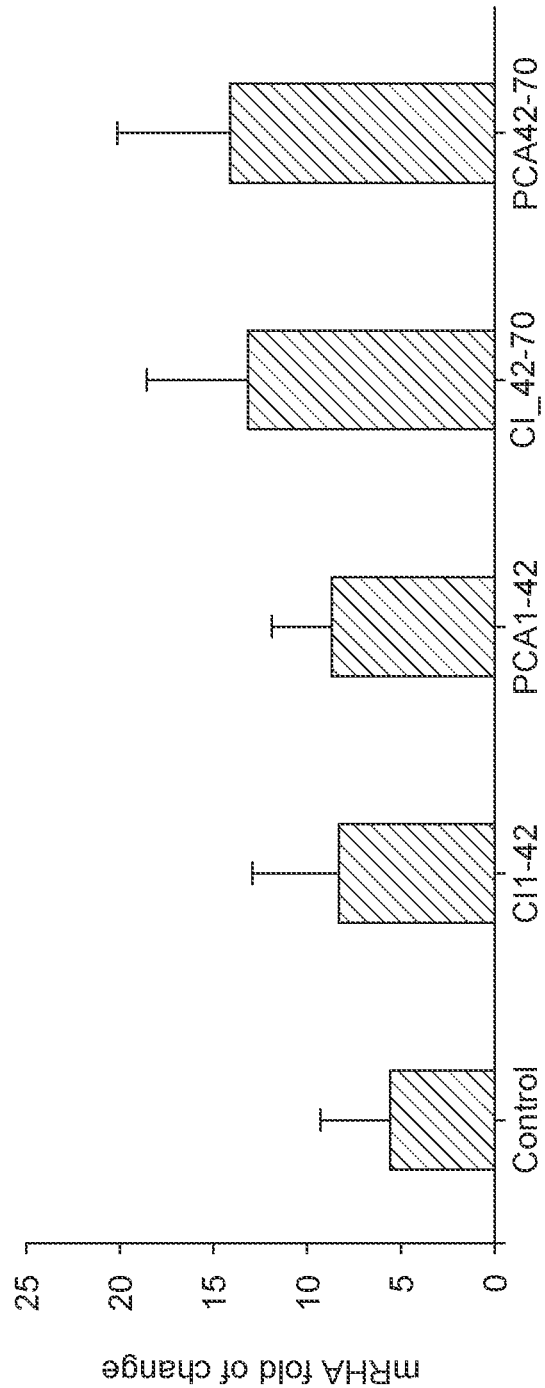
FIG. 20 shows increased expression of aggrecan in patellar cartilage of all four groups.
Figure 21:
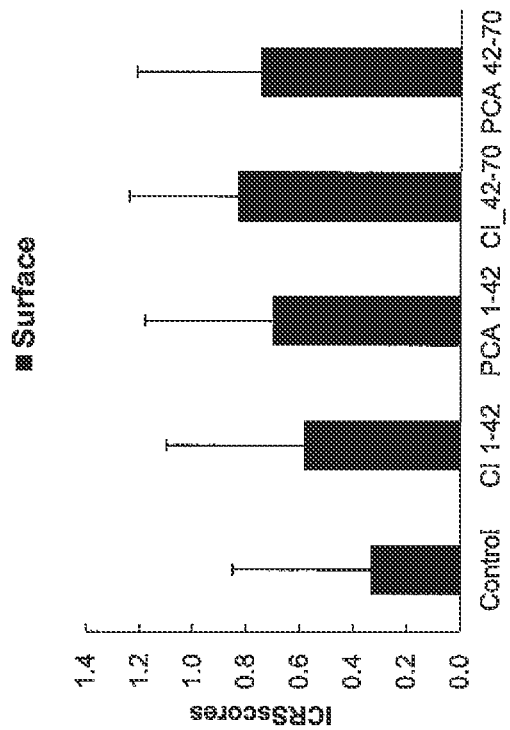
FIG. 21 provides a graph of ICRS histological visual scale scores for the surface of the cartilage. Scores for all four groups improved.
Figure 22:
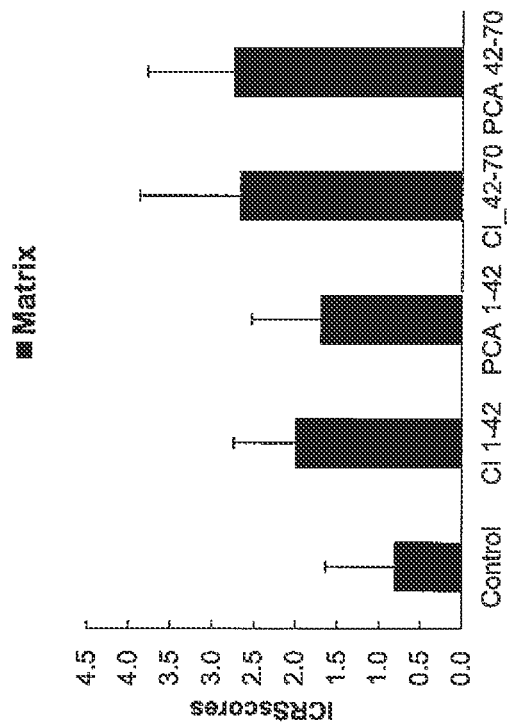
FIG. 22 provides a graph of ICRS histological visual scale scores for the cell matrix. Scores for all four groups improved.
Figure 23:
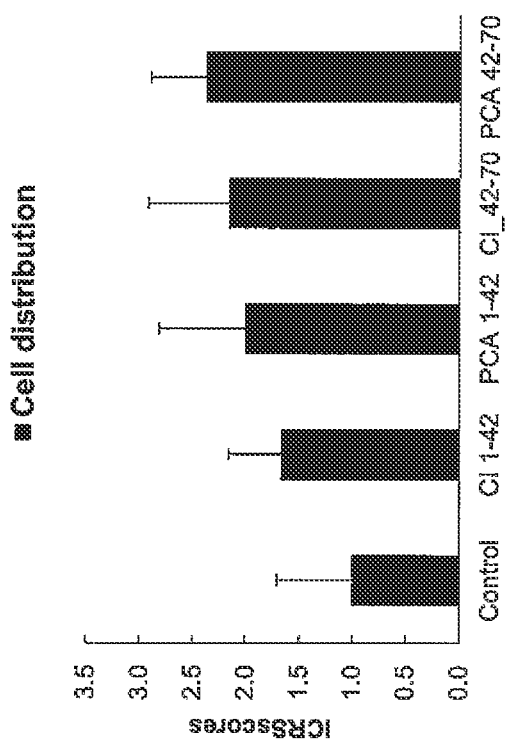
FIG. 23 provides a graph of ICRS histological visual scale scores for cell distribution. Cell distribution for all four groups improved.
Figure 24:
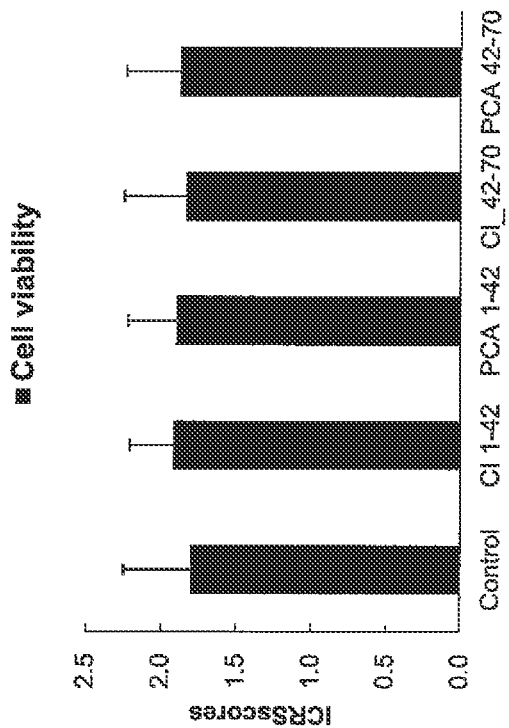
FIG. 24 provides a graph of ICRS histological visual scale scores for the cell viability. Cell viability remained the same for all four groups.
Figure 25:
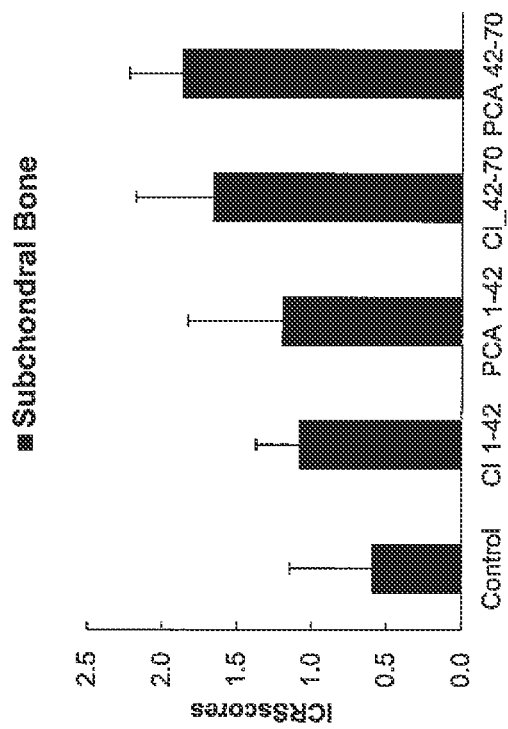
FIG. 25 provides a graph of ICRS histological visual scale scores for the subchondral bone. Scores for all four groups improved.
Figure 26:
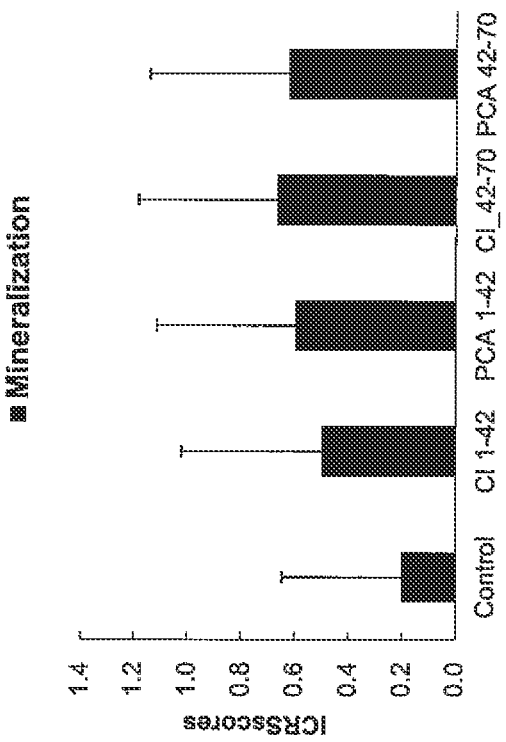
FIG. 26 provides a graph of ICRS histological visual scale scores for the Mineralization. Scores for all four groups improved.

FIG. 20 shows increased expression of aggrecan in patellar cartilage of all four groups.

White Blood Cell Studies—Anti-Inflammatory Effects

In addition to testing for the increase or decrease of various factors and cytokines, tests were run to count the number of white blood cells, including polymorphonuclear leukocytes (PMN), macrophages (Mac) and lymphocytes (Lym). Lymphocyte and macrophage cell numbers increase when there is inflammation, and they are involved in the release of catabolic cytokines that are released into the joint.

Figure 30:
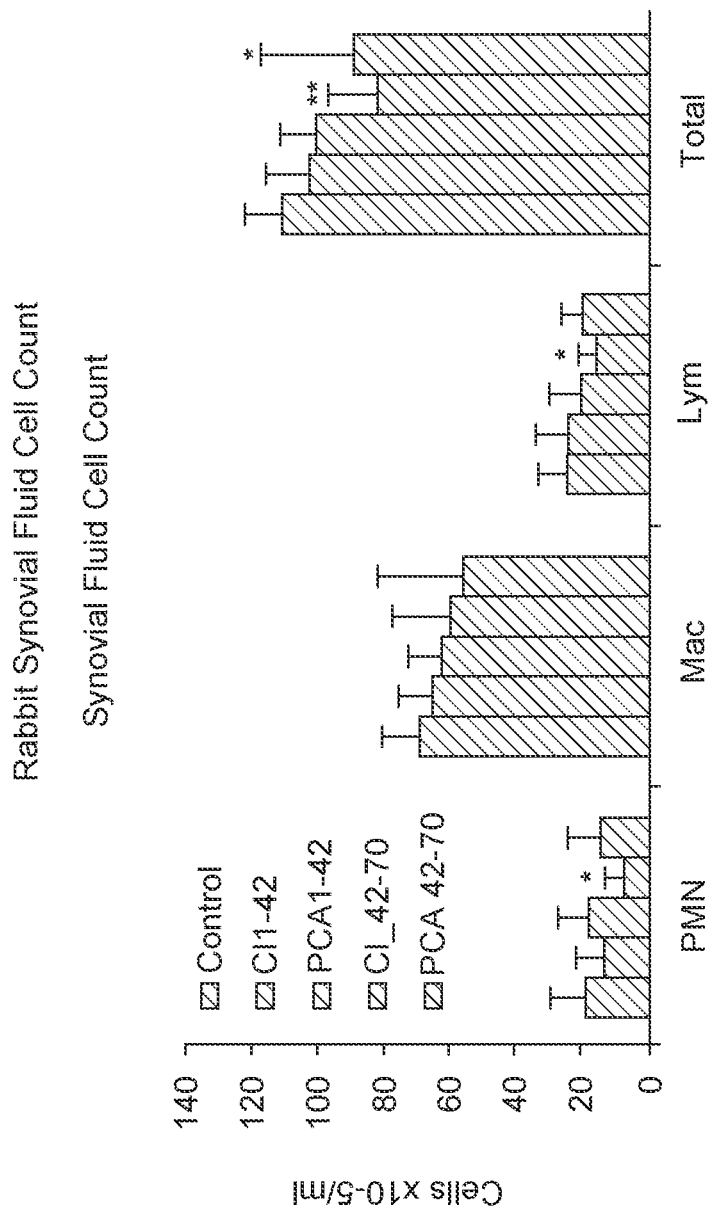
FIG. 30 shows that the total white blood cell count in the synovial fluid was decreased in all 4 study groups.
Figure 31A:
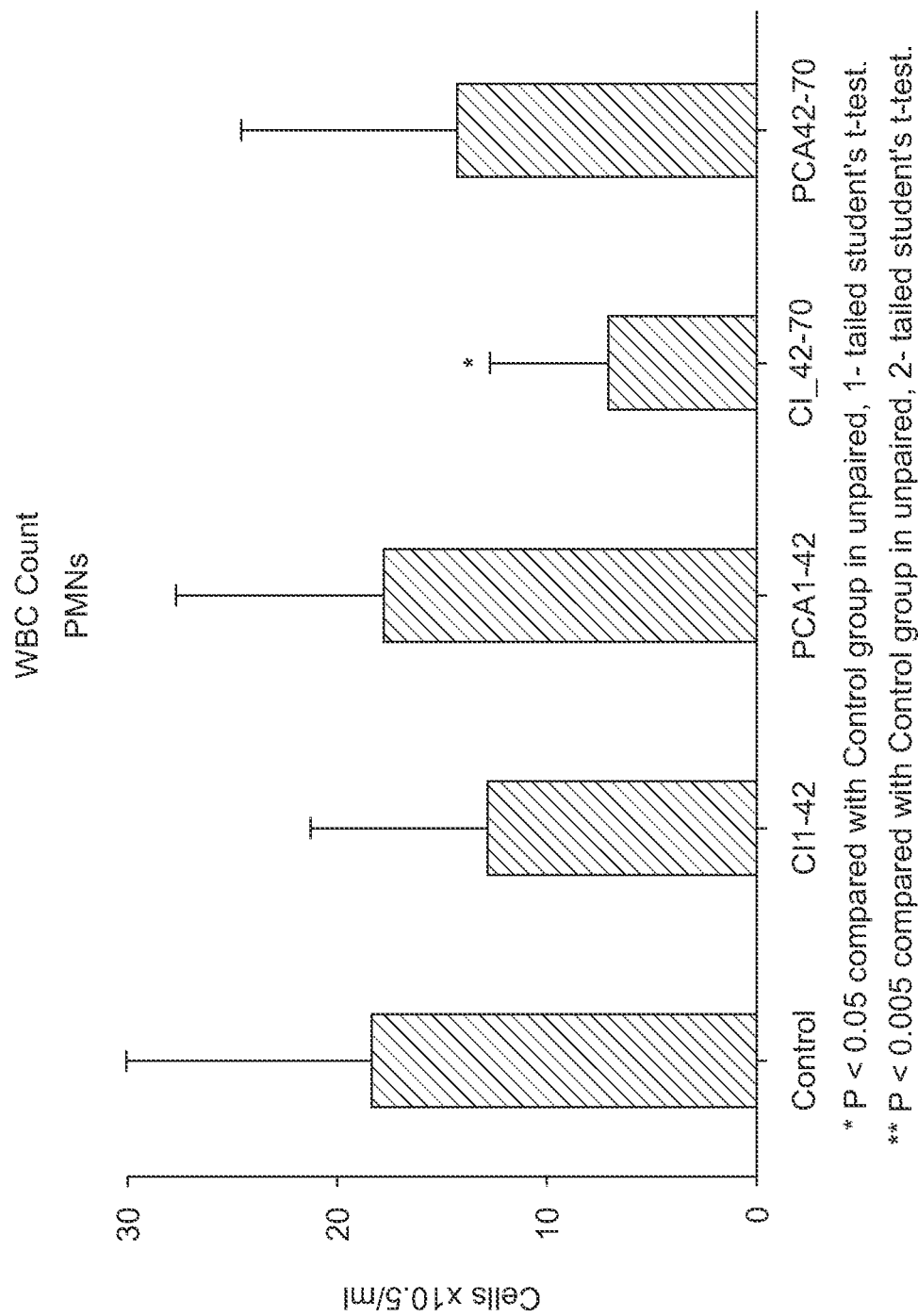
FIG. 31A shows that the number of PMN s was also reduced in the synovial fluid of all four groups, although most noticeable in the C3G groups.
Figure 31B:
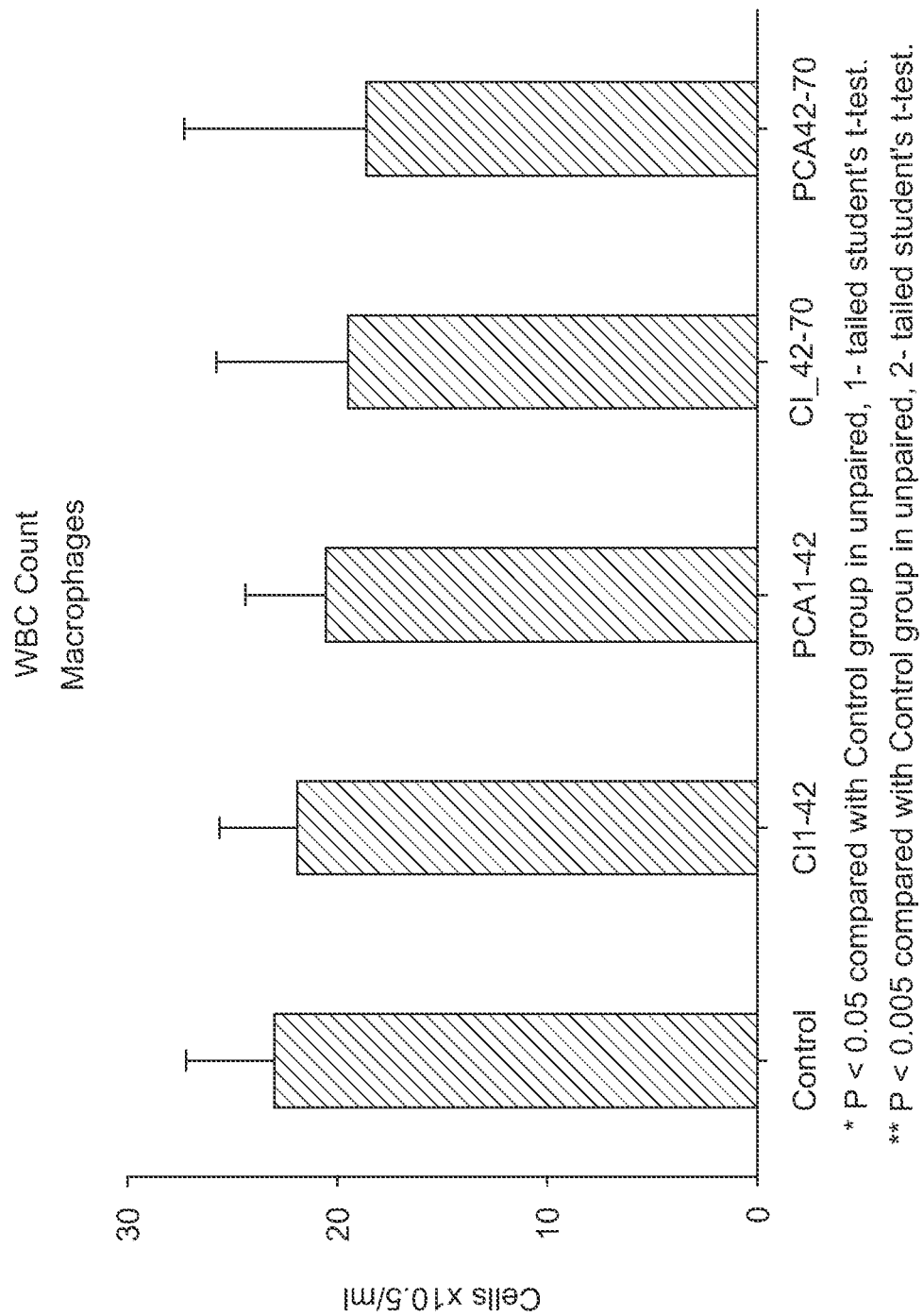
FIG. 31B shows that the number of macrophages was also decreased in all groups.
Figure 31C:
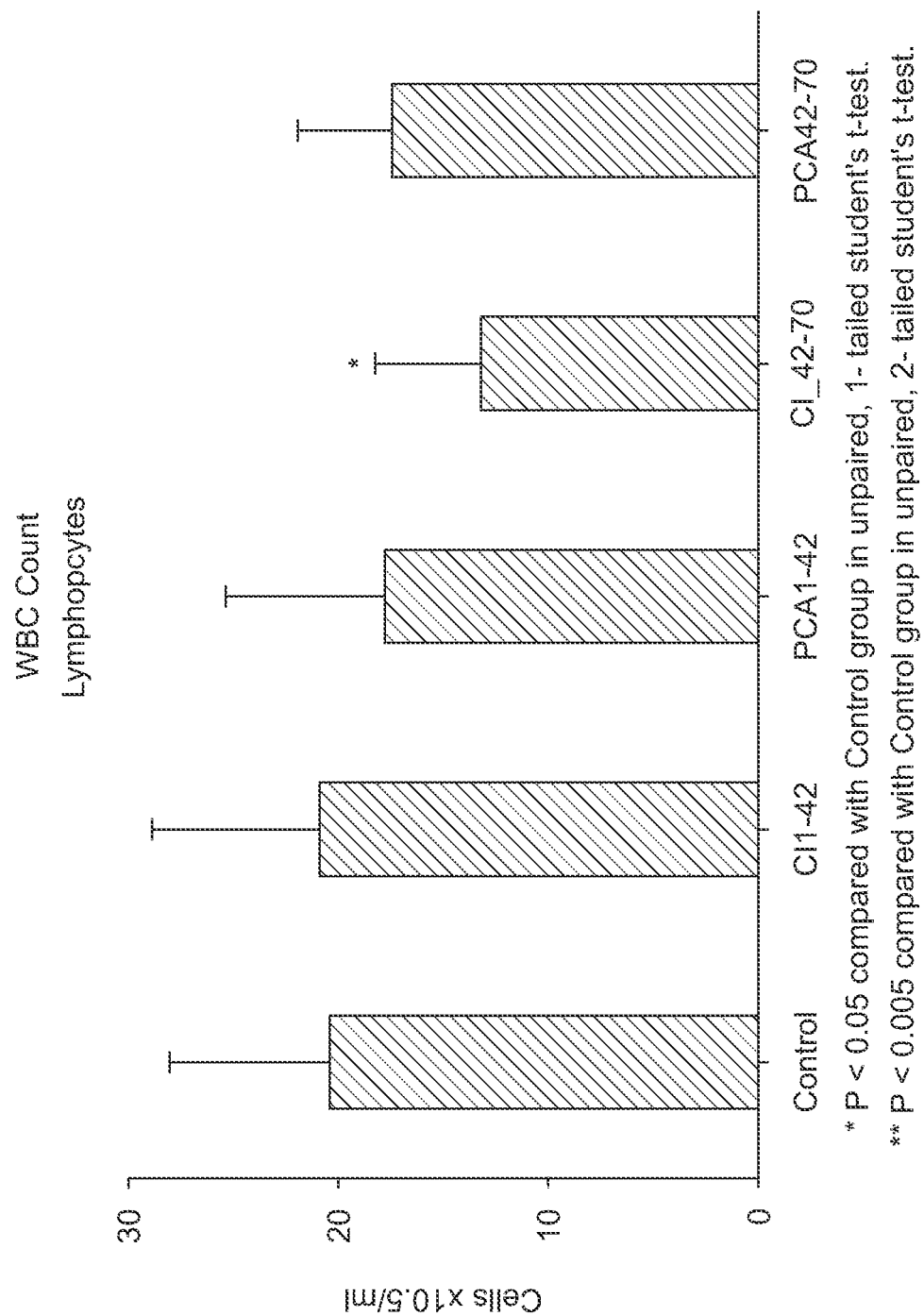
FIG. 31C shows that the number of lymphocytes in the synovial fluid was also decreased in 3 of the groups (both the G3G and PCT therapeutic group and the PCA prophylactic group).
Figure 31D:
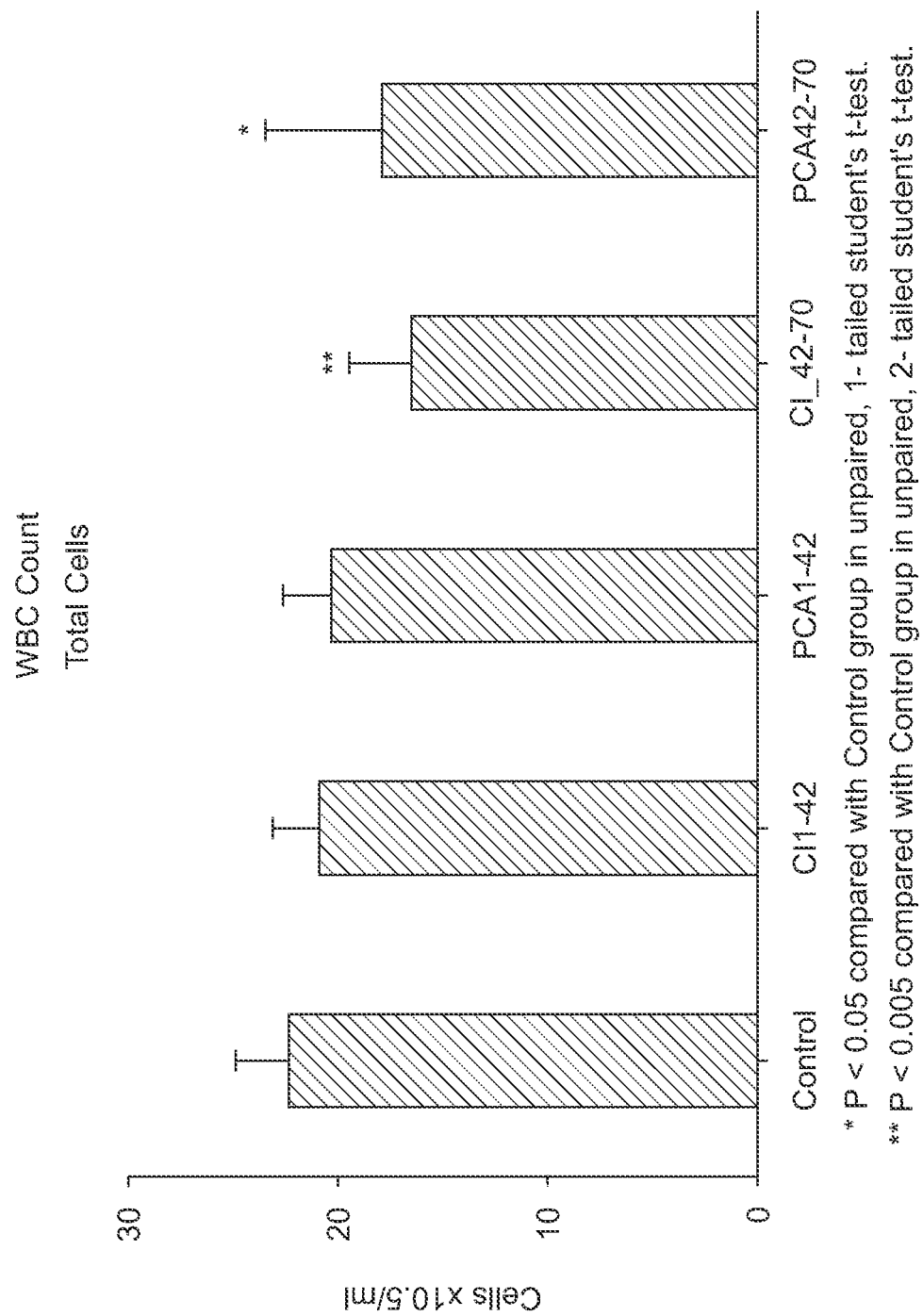
FIG. 31D shows that the total white blood cell count in the synovial fluid was decreased in all 4 study groups.
Figure 32A:
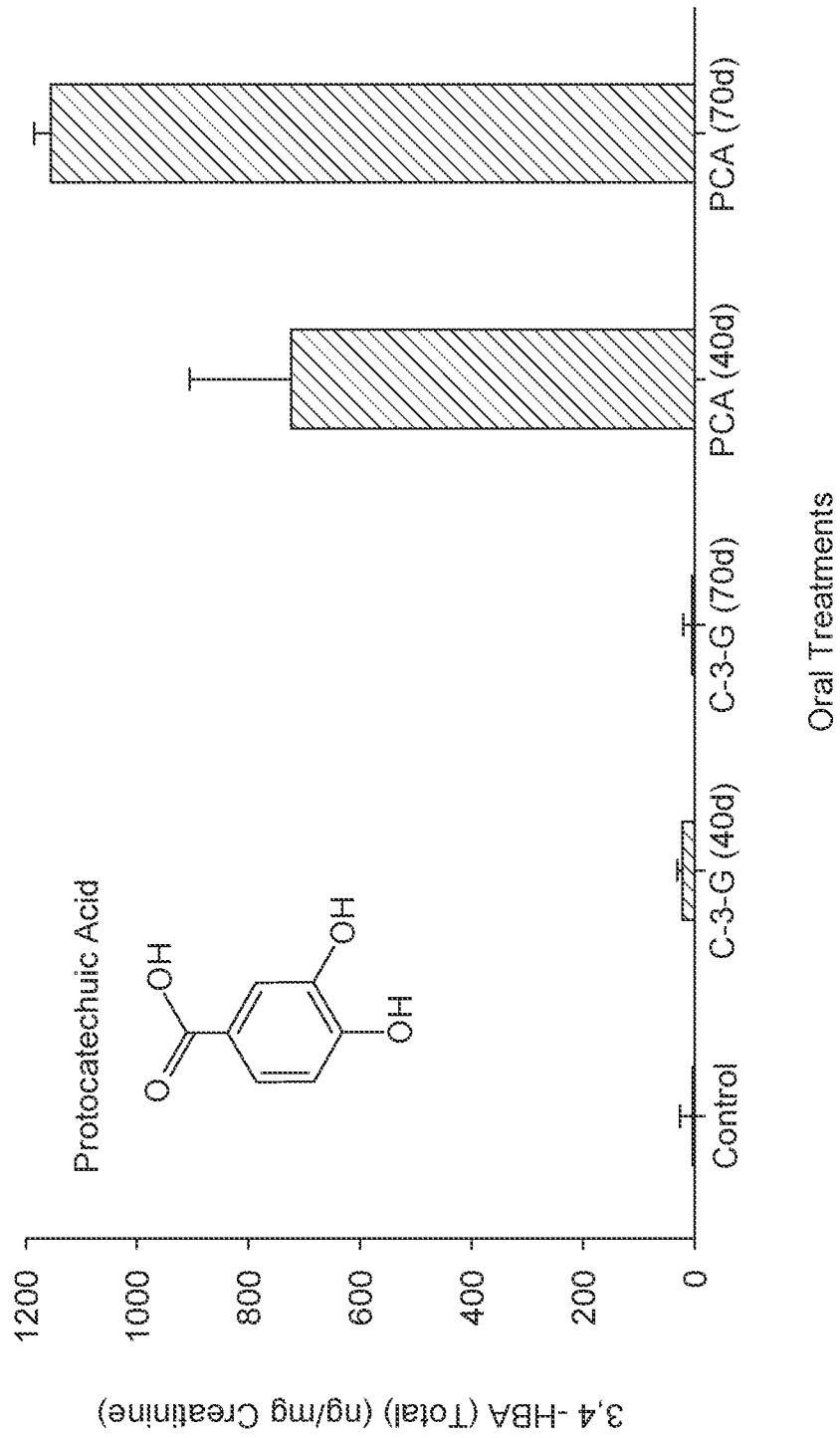
FIGS. 32A-C show Phenolic acid excretion in rabbits following oral gavage of control, cyanidin-3-glucoside (C-3-G)(30 mg/kg BW or Protocatechuic acid (3,4-dihydroxybenzoic acid)(26.4 mg/kg) expressed as micrograms per mg creatinine in the urine sample.
Figure 32B:
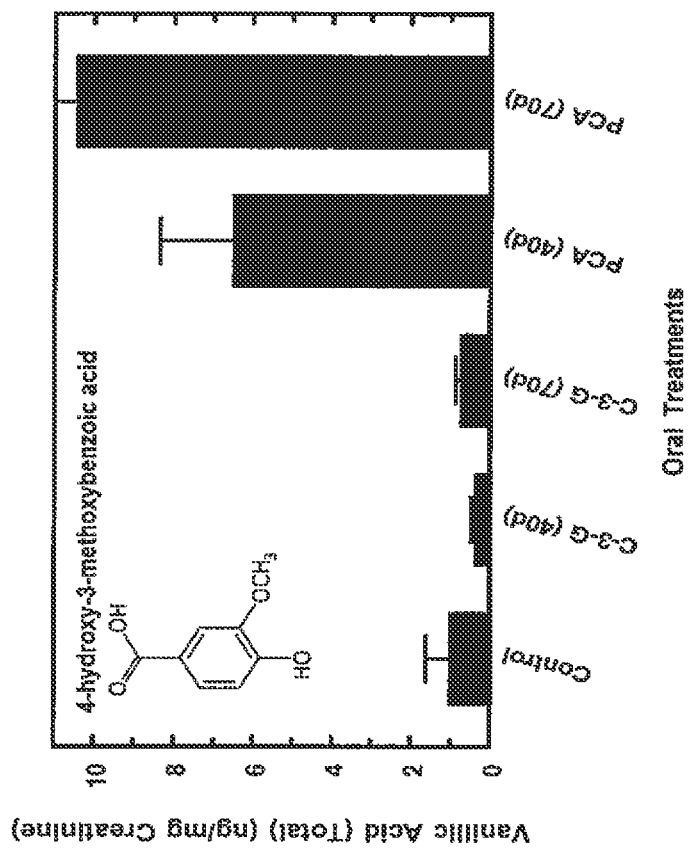
Figure 32C:
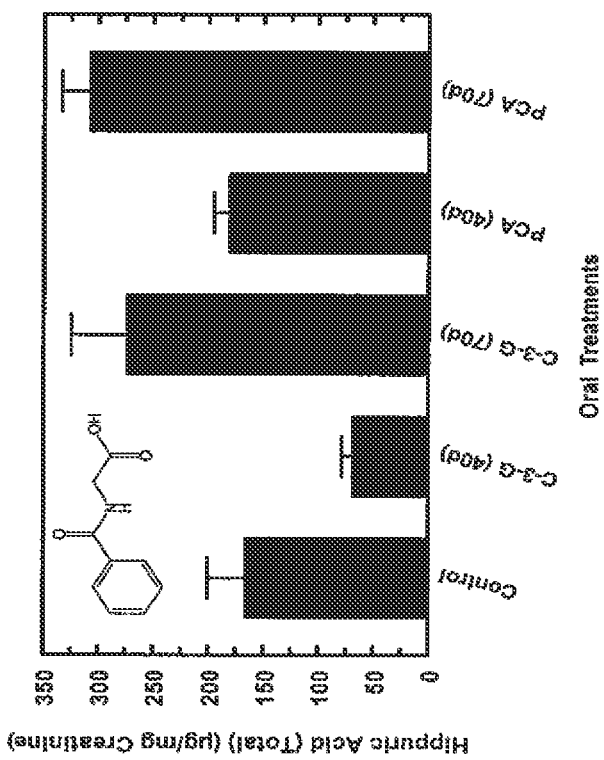

FIG. 30 and FIG. 31D show that the total white blood cell count in the synovial fluid was decreased in all 4 study groups as well as the numbers of macrophages was also decreased (see FIG. 31B). FIG. 31C shows that the number of lymphocytes in the synovial fluid was also decreased in 3 of the groups (both the PCA groups and the C3G therapeutic group). FIG. 31A shows that the number of PMN s was also reduced in the synovial fluid of all four groups, although most noticeable in the C3G groups.

Discussion

The hypothesis was confirmed. There was significant reduction in the inflammation as measured by the white blood count and differential cell count. The synovium showed enhancement of the anabolic genes with a corresponding inhibition of the catabolic genes. The synovial fluid reflected the alteration with an increase in anabolic cytokines and a corresponding decrease in catabolic cytokines. The articular cartilage responded with histochemical and ICRS histological scoring evidence of enhanced nutrition and resultant protection of the patellar articular cartilage from the treatments. Medial or lateral compartment cartilage were not studied because they were directly affected by the surgical procedure and the patella was spared from the surgical intervention.

The dosage given was effective for both C3G and PCA. The regimen of five times per week proved practical and effective. There was an apparent benefit seen in the results of the 6-week duration of the prophylactic group versus the shorter 4 week duration in the therapeutic groups. This may indicate a longer duration has greater potential for intra-articular change.

The failure of healing of the partial thickness lateral femoral condylar laceration was not unexpected. The duration of the study was short. The space within a laceration is minimal so as not to house or hold blood or cells. In addition, there is constant shearing motion of the laceration as well as weight bearing forces. Such healing would likely require addition of cells in a blood clot with immobilization to reduce the shearing forces and a much longer period of time for restoration. It has been reported that fibrocartilage repair existed for as long as six years and conversion to hyaline cartilage was seen at 20 years. Johnson L L, Delano M C, Spector M, Jeng L, Pittsley A, Gottschalk A. The biological response following autogenous bone grafting for large volume defects of the Knee: index surgery through 12-21-year follow-up. Cartilage Volume 3 Issue 1. January 2012. Pp 85-98. First published on Aug. 16, 2011, as DOI: 10.1177119476035114135 68.

Example 2: CRP Studies

C-reactive protein (CRP) is a protein found in the blood plasma, the levels of which rise in response to inflammation (i.e., C-reactive protein is an acute-phase protein). Its physiological role is to bind to phosphocholine expressed on the surface of dead or dying cells (and some types of bacteria) in order to activate the complement system via the C1Q complex. CRP rises within two hours of the onset of inflammation, up to a 50,000-fold, and peaks at 48 hours. Its half-life of 48 hours is constant, and therefore its level is determined by the rate of production and hence the severity of the precipitating cause. CRP is thus a screen for inflammation.

Knee surgery was performed to create a severe irreparable degenerative knee joint, which in turn elevated the CRP in the plasma to average of 8.8 mg/mL. A historical normal amount of CRP is 3.15 micrograms/mL. See Sun H, et al., Am J Pathol. October 2005; 167(4): 1139-1148. Rabbit CRP levels are close to the mean values of healthy middle-aged humans (2.82 mg/L) reported in the literature. See Ockene I S, et al., Clin Chem. 2001; 47:444-450.

The controls in the study were animals that had surgery and received no treatment. The prophylaxis test groups had the surgery and received 6 weeks of oral C-3-G or PCA 7 times per week as described in example 1. The therapeutic treatment group had surgery, received no treatment for 41 days and then at day 42 received oral C-3-G or PCA 7 times per week as described in example 1.

The CRP levels measured for the control group at 42 days (those receiving no treatment) showed an increase over normal levels: 8.8 mg/mL. The levels for the prophylaxis test group after treatment were reduced down to normal levels as follows:

Cyanidin-3-glucoside: CRP 3.1 micrograms/mL
Protocatechuic acid: CRP 3.6 micrograms/mL This shows that the initiation of the treatment at time zero did not allow the CRP to be elevated, in fact the levels decreased.

The therapeutic group had the surgery but received no treatment for 6 weeks and then received treatment for 4 weeks with same dosages of C3G or PCA that were used in the prophylaxis test groups. The plasma CRP levels the patients had very elevated levels. The plasma CRP was greatly elevated to 28.3 and 43 mg/mL (for the C3G and the PCA treatment groups, respectively). Thus, when the treatment was deferred for 6 weeks there was no effect on lowering the CRP, and in fact was elevated.

Thus, when C3G or PCA was given by oral route to a mammal immediately after injury, CRP, an indicator of inflammation was kept to normal levels (non-inflammatory levels).

While this disclosure includes specific examples, it will be apparent after an understanding of the disclosure of this application has been attained that various changes in form and details may be made in these examples without departing from the spirit and scope of the claims and their equivalents.

The invention claimed is:

1. A method of biological total joint replacement by arthroscopic surgery in a mammal comprising:
   arthroscopic surgically debriding diseased tissue and recontouring articular surfaces of a joint;
   orally administering a composition comprising a therapeutically effective amount of protocatechuic acid for between about 1 day and 1 month prior to arthroscopic surgically debriding the joint; and
   orally administering the composition comprising a therapeutically effective amount of protocatechuic acid for between 1 day and 6 months after arthroscopic surgically debriding the joint.

2. The method of claim 1, wherein the therapeutically effective amount comprises a daily dosage ranging from 0.035 to 0.300 millimoles protocatechuic acid per kilogram of body weight.

3. The method of claim 2, wherein the composition comprises a tablet, a pill, a capsule, or a liquid composition comprising water.

4. The method of claim 3, wherein the tablet, the pill, or the capsule comprise about 500 mg of protocatechuic acid.

5. The method of claim 1, wherein the administration of the composition is done for between 1 and 6 days prior to surgically debriding the joint.

6. The method of claim 1, wherein the administration of the composition is done for between 1 day and 10 weeks after surgically debriding the joint.

7. The method of claim 1, wherein the daily dose is between about 0.100 mmoles and about 0.200 mmoles protocatechuic acid per kg body weight.

8. The method of claim 1, wherein the composition further comprises zinc.

9. The method of claim 8, wherein zinc comprises zinc sulfate or zinc oxide.

10. The method of claim 1, wherein the oral administration of protocatechuic acid produces a chondroreparative or chondrorestorative effect.

11. The method of claim 1, wherein the oral administration of protocatechuic acid produces bone regeneration or repair.

12. The method of claim 1, wherein the oral administration of protocatechuic acid produces synovial regeneration or repair.

13. A method of biological total joint replacement by arthroscopic surgery in a mammal consisting essentially of the steps:
- arthroscopic surgically debriding diseased tissue and recontouring articular surfaces of a joint;
- orally administering a composition comprising a therapeutically effective amount of protocatechuic acid for between about 1 day and 1 month prior to arthroscopic surgically debriding the joint; and
- orally administering the composition comprising a therapeutically effective amount of protocatechuic acid for between 1 day and 6 months after arthroscopic surgically debriding the joint.

\* \* \* \* \*